United States Patent [19]

Donovan et al.

[11] Patent Number: 5,382,429

[45] Date of Patent: Jan. 17, 1995

[54] BACILLUS THURINGIENSIS PROTEIN TOXIC TO COLEOPTERAN INSECTS

[75] Inventors: William P. Donovan, Levittown, Pa.; Mark J. Rupar, Wilmington, Del.; Annette C. Slaney, Hamilton Square, N.J.; Timothy B. Johnson, Langhorne, Pa.

[73] Assignee: Ecogen Inc., Langhorne, Pa.

[21] Appl. No.: 950,352

[22] Filed: Sep. 24, 1992

Related U.S. Application Data

[62] Division of Ser. No. 496,568, Mar. 20, 1990, Pat. No. 5,187,091.

[51] Int. Cl.⁶ .................... C12N 15/00; A01N 63/00; C07K 13/00
[52] U.S. Cl. .................... 424/93.461; 435/252.1; 435/252.31; 435/713; 435/172.3; 424/195.1; 530/350; 530/820; 514/12
[58] Field of Search .................... 424/93 L, 195.1; 435/252.1, 252.31, 71.3; 536/23.7; 935/72; 530/350, 820; 514/12

[56] References Cited

U.S. PATENT DOCUMENTS

| | | | |
|---|---|---|---|
| 4,695,455 | 9/1987 | Barius et al. | 424/93 D |
| 4,766,203 | 8/1988 | Krieg et al. | 530/370 |
| 4,771,131 | 9/1988 | Herrnstadt et al. | 536/23.71 |
| 4,797,279 | 1/1989 | Karamata et al. | 424/93 R |
| 4,910,016 | 3/1990 | Gaertner et al. | 424/93 L |
| 4,966,765 | 10/1990 | Payne et al. | 424/93 L |
| 4,996,155 | 2/1991 | Sick et al. | 435/252.3 |
| 4,999,192 | 3/1991 | Payne et al. | 424/93 L |
| 5,006,336 | 4/1991 | Payne | 424/93 L |
| 5,024,837 | 6/1991 | Donovan et al. | 424/93 A |
| 5,055,293 | 10/1991 | Aronson et al. | 424/93 K |

FOREIGN PATENT DOCUMENTS

| | | |
|---|---|---|
| 289479 | 11/1988 | European Pat. Off. |
| 318143 | 5/1989 | European Pat. Off. |
| 324254 | 7/1989 | European Pat. Off. |
| 328383 | 8/1989 | European Pat. Off. |
| 337604 | 10/1989 | European Pat. Off. |
| 346114 | 12/1989 | European Pat. Off. |
| 382990 | 8/1990 | European Pat. Off. |
| 9013651 | 11/1990 | WIPO |
| 9107481 | 5/1991 | WIPO |
| 9114778 | 10/1991 | WIPO |
| 9116433 | 10/1991 | WIPO |
| 9213954 | 8/1992 | WIPO |

OTHER PUBLICATIONS

Lambert et al., *Gene* 110 pp. 131–132 (1992) "Nucleotide sequence of gene *cryIIID* encoding a novel coleopteran-active crystal protein from strain BTI109P of *Bacillus thuringiensis* subsp. *kurstaki*".

Lambert et al., *Appl. Environ. Microbiol.* 58 pp. 2536–2542 (Aug. 1992) "Novel *Bacillus thuringiensis* Insecticidal Crystal Protein with a Silent Activity against Coleopteran Larvae".

Cidaira et al., *FEMS Microbiol. Lett.* 81 pp. 129–134 (1991), "A novel strain of *Bacillus thruingiensis* (NCIMB 40152) active against coleopteran insects".

Crickmore et al., *Biochem. J.* 270 pp. 133–136 (1990), "The construction of *Bacillus thuringiensis* strains expressing novel entomocidal δ-endotoxin combinations."

Sick et al., *Nucleic Acids Res.* 18, p. 1305 (1990) "Nucleotide sequence of a coleopteran-active toxin gene from a new isolate of *Bacillus thuringiensis* subsp. *tolworthi*".

Höfte et al., *Microbiol. Rev.* 53, pp. 242–255 (1989) "Insecticidal Crystal Proteins of *Bacillus thuringiensis*".

(List continued on next page.)

*Primary Examiner*—Richard A. Schwartz
*Assistant Examiner*—Gary L. Brown
*Attorney, Agent, or Firm*—Christopher Egolf; Alan S. Nadel

[57] ABSTRACT

A purified and isolated cryIII-type gene was obtained from a novel B.t. strain. The gene has a nucleotide base sequence coding for the amino acid sequence illustrated in FIG. 1. The 74.4 kDa protein produced by this gene is an irregularly shaped crystal that is toxic to coleopteran insects, including Colorado potato beetle and insects of the genus Diabrotica.

7 Claims, 8 Drawing Sheets

OTHER PUBLICATIONS

Donovan et al., *Mol. Gen. Genet.*, 214, pp. 365–372 (1988) "Isolation and characterization of EG 2158, a new strain of *Bacillus thuringiensis* toxic to coleopteran larvae, and nucleotide sequence of the toxin gene".

McPherson et al., *Bio/Technology*, 6, pp. 61-66 (1988) "Characterization of the Coleopteran-Specific Protein Gene of *Bacillus thuringiensis* var. *tenebrionis*".

Sekar, *Current Microbiology*, 17, pp. 347-349 (1988), "The Insecticidal Crystal Protein Gene Is Expressed in Vegetative Cells of *Bacillus thuringiensis* var. *tenebrionis*".

Delecluse et al., *Mol. Gen. Genet.*, 214, pp. 42-47 (1988), "Specificity of action on mosquito larvae of *Bacillus thuringiensis israelensis* toxins encoded by two different genes".

Jahn et al., *FEMS Microbiol. Lett.*, 48, pp. 311-315 (1988), "Cloning of an insecticidal toxin gene of *Bacillus turingiensis* subsp. *tenebrionis* and its expression in *Escherichia coli* cells".

Sekar et al., *Proc. Natl. Acad. Sci. USA*, 84, pp. 7036-7040 (1987) "Molecular cloning and characterization of the insecticidal crystal protein gene of *Bacillus thuringiensis* var. *tenebrionis*".

Höfte et al., *Nucleic Acids Research*, 15, pp. 7183 (1987) "Nucleotide sequence of a gene encoding an insecticidal protein of *Bacillus thuringiensis* var. *tenebrionsis* toxic against Coleoptera".

Herrnstadt et al., *Gene*, 57, pp. 37-46 (1987) "Nucleotide sequence and deduced amino acid sequence of a coleopteran-active delta-endotoxin gene from *Bacillus thuringiensis* subsp. *san diego*".

Krieg et al., *J. Appl. Ent.*, 104, pp. 417-424 (1987) "'*Bacillus thuringiensis* var. *san diego*' Stamm M-7 ist identisch mit dem zuvor in Deutschland isolierten kaferwirksamen *B. thuringiensis* subsp. *tenebrionis* Stamm BI 256-82".

Herrnstadt et al., *Bio/Technology*, 4, pp. 305-308 (1986) "A new strain of *Bacillus thuringiensis* with activity against coleopteran insects".

Bernhard, *FEMS Microbiol. Lett.*, 33, pp. 261-265 (1986) "Studies on the delta-endotoxin of *Bacillus thuringiensis* var. *tenebrionis*".

Wu et al., *FEBS Lett.*, 190, pp. 232-236 (1985), "Synergism in mosquitocidal activity of 26 and 65 kDa proteins from *Bacillus thuringiensis* subsp. *israelensis* crystals."

Marrone et al., *J. Econ. Entomol.*, 78, pp. 290-293 (1985) "Improvements in Laboratory Rearing of the Southern Corn Rootworm, *Diabrotica undecimpuncta nowardi* Barber (Coleoptera: Chrysomelidae), on an Artificial Diet and Corn".

Krieg et al., *Anz. Schaedlingskde., Pflanzenchutz, Umweltschutz*, 57, pp. 145-150 (1984) "Neue Ergebnisse Uber *Bacillus thuringiensis* var. *tenebrionis* unter besonderer Berücksichtigung seiner Wirkung auf den Kartoffelkäfer (*Leptinotarsa decemlineata*)".

Korn et al., *DNA*, 3, pp. 421-436, (1984) "Analysis of Biological Sequences on Small Computers".

Krieg et al., *A. Agnew. Ent.*, 96, pp. 500-508 (1983) (with translation) "*Bacillus thuringiensis* var. *tenebrionis*: a new pathotype effective against larvae of Coleoptera".

Marinus et al., *Mol. Gen. Genet.*, 192, pp. 288-289 (1983) "Insertion Mutations in the *dam* gene of *Escherichia coli* K-12".

Southern, *J. Molec. Biol.*, 98, pp. 503-517 (1975) "Detection of Specific sequences among DNA fragments separated by Gel Electrophoresis".

Daum, *Bull. Entomol. Soc. Am.*, 16, pp. 10-15 (1970) "Revision of two computer programs for Probit analysis".

Abbott, *J. Econ. Entomol.*, 18, pp. 265-267 (1925) "A method of computing the effectiveness of an insecticide".

Figure 1a

```
         10        20        30        40        50        60
GGGAGGAAGAAAAATGAATCCAAACAATCGAAGTGAACATGATACGATAAAGGTTACACC
 RBS          MetAsnProAsnAsnArgSerGluHisAspThrIleLysValThrPr 70        80        90       100       110       120
TAACAGTGAATTGCAAACTAACCATAATCAATATCCTTTAGCTGACAATCCAAATTCAAC
oAsnSerGluLeuGlnThrAsnHisAsnGlnTyrProLeuAlaAspAsnProAsnSerTh 130       140       150       160       170       180
ACTAGAAGAATTAAATTATAAAGAATTTTTAAGAATGACTGAAGACAGTTCTACGGAAGT
rLeuGluGluLeuAsnTyrLysGluPheLeuArgMetThrGluAspSerSerThrGluVa 190       200       210       220       230       240
GCTAGACAACTCTACAGTAAAAGATGCAGTTGGGACAGGAATTTCTGTTGTAGGGCAGAT
lLeuAspAsnSerThrValLysAspAlaValGlyThrGlyIleSerValValGlyGlnIl 250       260       270       280       290       300
TTTAGGTGTTGTAGGAGTTCCATTTGCTGGGGCACTCACTTCATTTATCAATCATTTCT
eLeuGlyValValGlyValProPheAlaGlyAlaLeuThrSerPheTyrGlnSerPheLe 310       320       330       340       350       360
TAACACTATATGGCCAAGTGATGCTGACCCATGGAAGGCTTTTATGGCACAAGTTGAAGT
uAsnThrIleTrpProSerAspAlaAspProTrpLysAlaPheMetAlaGlnValGluVa 370       380       390       400       410       420
ACTGATAGATAAGAAAATAGAGGAGTATGCTAAAAGTAAAGCTCTTGCAGAGTTACAGGG
lLeuIleAspLysLysIleGluGluTyrAlaLysSerLysAlaLeuAlaGluLeuGlnGl 430       440       450       460       470       480
TCTTCAAAATAATTTCGAAGATTATGTTAATGCGTTAAATTCCTGGAAGAAAACACCTTT
yLeuGlnAsnAsnPheGluAspTyrValAsnAlaLeuAsnSerTrpLysLysThrProLe 490       500       510       520       530       540
AAGTTTGCGAAGTAAAAGAAGCCAAGATCGAATAAGGGAACTTTTTTCTCAAGCAGAAAG
uSerLeuArgSerLysArgSerGlnAspArgIleArgGluLeuPheSerGlnAlaGluSe 550       560       570       580       590       600
TCATTTTCGTAATTCCATGCCGTCATTTGCAGTTTCCAAATTCGAAGTGCTGTTTCTACC
rHisPheArgAsnSerMetProSerPheAlaValSerLysPheGluValLeuPheLeuPr 610       620       630       640       650       660
AACATATGCACAAGCTGCAAATACACATTTATTGCTATTAAAAGATGCTCAAGTTTTTGG
oThrTyrAlaGlnAlaAlaAsnThrHisLeuLeuLeuLeuLysAspAlaGlnValPheGl 670       680       690       700       710       720
AGAAGAATGGGGATATTCTTCAGAAGATGTTGCTGAATTTTATCATAGACAATTAAAACT
yGluGluTrpGlyTyrSerSerGluAspValAlaGluPheTyrHisArgGlnLeuLysLe 730       740       750       760       770       780
TACACAACAATACACTGACCATTGTGTTAATTGGTATAATGTTGGATTAAATGGTTTAAG
uThrGlnGlnTyrThrAspHisCysValAsnTrpTyrAsnValGlyLeuAsnGlyLeuAr 790       800       810       820       830       840
AGGTTCAACTTATGATGCATGGGTCAAATTTAACCGTTTTCGCAGAGAAATGACTTTAAC
gGlySerThrTyrAspAlaTrpValLysPheAsnArgPheArgArgGluMetThrLeuTh 850       860       870       880       890       900
TGTATTAGATCTAATTGTACTTTTCCCATTTTATGATATTCGGTTATACTCAAAAGGGGT
rValLeuAspLeuIleValLeuPheProPheTyrAspIleArgLeuTyrSerLysGlyVa
```

FIGURE 1B

```
          910       920       930       940       950       960
     TAAAACAGAACTAACAAGAGACATTTTTACGGATCCAATTTTTTCACTTAATACTCTTCA
     lLysThrGluLeuThrArgAspIlePheThrAspProIlePheSerLeuAsnThrLeuGl
                                       BamHI
          970       980       990      1000      1010      1020
     GGAGTATGGACCAACTTTTTTGAGTATAGAAAACTCTATTCGAAAACCTCATTTATTTGA
     nGluTyrGlyProThrPheLeuSerIleGluAsnSerIleArgLysProHisLeuPheAs 1030      1040      1050      1060      1070      1080
     TTATTTACAGGGGATTGAATTTCATACGCGTCTTCAACCTGGTTACTTTGGGAAAGATTC
     pTyrLeuGlnGlyIleGluPheHisThrArgLeuGlnProGlyTyrPheGlyLysAspSe 1090      1100      1110      1120      1130      1140
     TTTCAATTATTGGTCTGGTAATTATGTAGAAACTAGACCTAGTATAGGATCTAGTAAGAC
     rPheAsnTyrTrpSerGlyAsnTyrValGluThrArgProSerIleGlySerSerLysTh 1150      1160      1170      1180      1190      1200
     AATTACTTCCCCATTTTATGGAGATAAATCTACTGAACCTGTACAAAAGCTAAGCTTTGA
     rIleThrSerProPheTyrGlyAspLysSerThrGluProValGlnLysLeuSerPheAs
                                                         HindIII
         1210      1220      1230      1240      1250      1260
     TGGACAAAAAGTTTATCGAACTATAGCTAATACAGACGTAGCGGCTTGGCCGAATGGTAA
     pGlyGlnLysValTyrArgThrIleAlaAsnThrAspValAlaAlaTrpProAsnGlyLy 1270      1280      1290      1300      1310      1320
     GGTATATTTAGGTGTTACGAAAGTTGATTTTAGTCAATATGATGATCAAAAAAATGAAAC
     sValTyrLeuGlyValThrLysValAspPheSerGlnTyrAspAspGlnLysAsnGluTh 1330      1340      1350      1360      1370      1380
     TAGTACACAAACATATGATTCAAAAAGAAACAATGGCCATGTAAGTGCACAGGATTCTAT
     rSerThrGlnThrTyrAspSerLysArgAsnAsnGlyHisValSerAlaGlnAspSerIl 1390      1400      1410      1420      1430      1440
     TGACCAATTACCGCCAGAAACAACAGATGAACCACTTGAAAAAGCATATAGTCATCAGCT
     eAspGlnLeuProProGluThrThrAspGluProLeuGluLysAlaTyrSerHisGlnLe 1450      1460      1470      1480      1490      1500
     TAATTACGCGGAATGTTTCTTAATGCAGGACCGTCGTGGAACAATTCCATTTTTTACTTG
     uAsnTyrAlaGluCysPheLeuMetGlnAspArgArgGlyThrIleProPhePheThrTr 1510      1520      1530      1540      1550      1560
     GACACATAGAAGTGTAGACTTTTTTAATACAATTGATGCTGAAAAGATTACTCAACTTCC
     pThrHisArgSerValAspPhePheAsnThrIleAspAlaGluLysIleThrGlnLeuPr 1570      1580      1590      1600      1610      1620
     AGTAGTGAAAGCATATGCCTTGTCTTCAGGTGCTTCCATTATTGAAGGTCCAGGATTCAC
     oValValLysAlaTyrAlaLeuSerSerGlyAlaSerIleIleGluGlyProGlyPheTh 1630      1640      1650      1660      1670      1680
     AGGAGGAAATTTACTATTCCTAAAAGAATCTAGTAATTCAATTGCTAAATTTAAAGTTAC
     rGlyGlyAsnLeuLeuPheLeuLysGluSerSerAsnSerIleAlaLysPheLysValTh 1690      1700      1710      1720      1730      1740
     ATTAAATTCAGCAGCCTTGTTACAACGATATCGTGTAAGAATACGCTATGCTTCTACCAC
     rLeuAsnSerAlaAlaLeuLeuGlnArgTyrArgValArgIleArgTyrAlaSerThrTh 1750      1760      1770      1780      1790      1800
     TAACTTACGACTTTTTGTGCAAAATTCAAACAATGATTTTCTTGTCATCTACATTAATAA
     rAsnLeuArgLeuPheValGlnAsnSerAsnAsnAspPheLeuValIleTyrIleAsnLy
```

FIGURE 1c

```
        1810       1820       1830       1840       1850       1860
AACTATGAATAAAGATGATGATTTAACATATCAAACATTTGATCTCGCAACTACTAATTC
sThrMetAsnLysAspAspAspLeuThrTyrGlnThrPheAspLeuAlaThrThrAsnSe 1870       1880       1890       1900       1910       1920
TAATATGGGGTTCTCGGGTGATAAGAATGAACTTATAATAGGAGCAGAATCTTTCGTTTC
rAsnMetGlyPheSerGlyAspLysAsnGluLeuIleIleGlyAlaGluSerPheValSe 1930       1940       1950       1960       1970
TAATGAAAAAATCTATATAGATAAGATAGAATTTATCCCAGTACAATTGTAA
rAsnGluLysIleTyrIleAspLysIleGluPheIleProValGlnLeuEnd
```

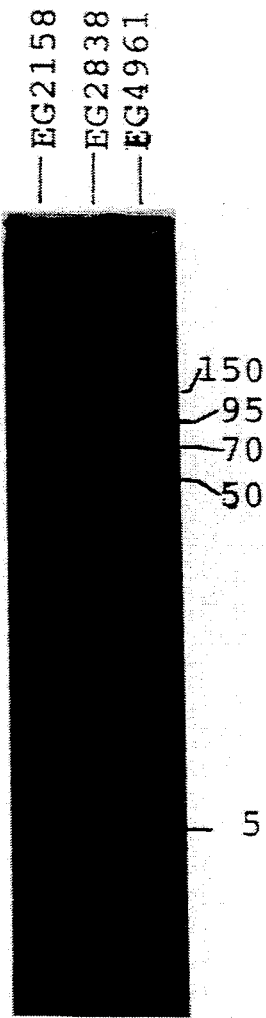
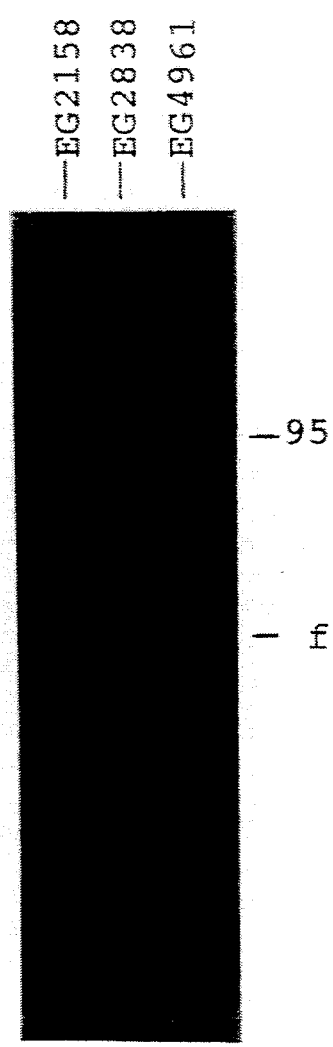
FIG. 2
FIG. 3

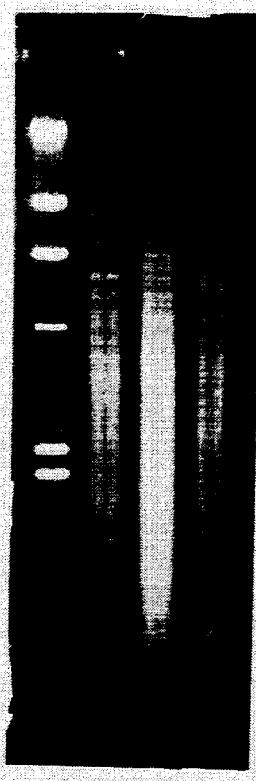 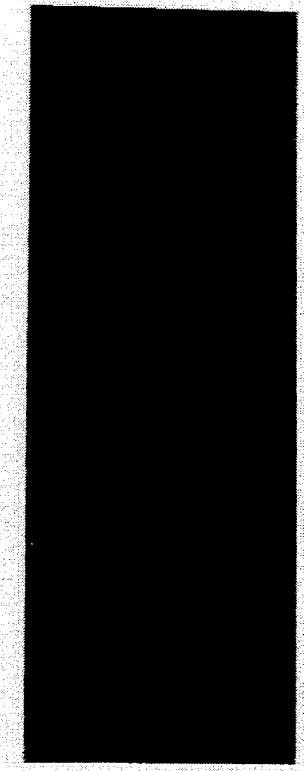
FIG. 4     FIG. 5

BACILLUS THURINGIENSIS PROTEIN TOXIC TO COLEOPTERAN INSECTS

CROSS REFERENCE TO THE RELATED APPLICATION

This application is a division of application Ser. No. 07/496,568, filed Mar. 20, 1990, now U.S. Pat. No. 5,187,091.

FIELD OF THE INVENTION

The present invention relates to a gene isolated from *Bacillus thuringiensis* (hereinafter "*B.t.*") encoding an insecticidal crystal protein designated CryIIIC, as well as insecticidal compositions containing the protein and plants transformed with the gene. The insecticidal compositions and transformed plants are toxic to insects of the order Coleoptera, and are particularly toxic to insects of the genus Diabrotica.

BACKGROUND OF THE INVENTION

*B.t.* is a gram-positive soil bacterium that produces crystal proteins during sporulation which are specifically toxic to certain orders and species of insects. Many different strains of *B.t.* have been shown to produce insecticidal crystal proteins. Compositions including *B.t.* strains which produce insecticidal proteins have been commercially available and used as environmentally acceptable insecticides because they are quite toxic to the specific target insect, but are harmless to plants and other non-targeted organisms.

A number of genes encoding crystal proteins have been cloned from several strains of *B.t.* A good overview is set forth in H. Hofte et al., *Microbiol. Rev.*, 53, pp. 242–255 (1989). While this reference is not prior art with respect to the present invention, it provides a good overview of the genes and proteins obtained from *B.t.* and their uses, adopts a nomenclature and classification scheme for *B.t.* genes and proteins, and has an extensive bibliography.

The *B.t.* crystal protein is active in the insect only after ingestion. After ingestion by an insect, the alkaline pH and proteolytic enzymes in the mid-gut solubilize the crystal allowing the release of the toxic components. These toxic components disrupt the mid-gut cells causing the insect to cease feeding and, eventually, to die. In fact, *B.t.* has proven to be an effective and environmentally safe insecticide in dealing with various insect pests.

As noted by Hofte et al., the majority of insecticidal *B.t.* strains are active against insects of the order Lepidoptera, i.e., caterpillar insects. Other *B.t.* strains are insecticidally active against insects of the order Diptera, i.e., flies and mosquitoes, or against both lepidopteran and dipteran insects. In recent years, a few *B.t.* strains have been reported as producing crystal protein that is insecticidal to insects of the order Coleoptera, i.e., beetles.

The first isolation of a coleopteran-toxic *B.t.* strain is reported by A. Krieg et al., in *Z. angew. Ent.*, 96, pp. 500–508 (1983); see also A. Krieg et al., *Anz. Schaedlingskde, Pflanzenschutz, Umweltschutz*, 57, pp. 145–150 (1984) and U.S. Pat. No. 4,766,203, issued Aug. 23, 1988 of A. Krieg et al. The strain, designated *B.t.* var. *tenebrionis*, is reported to be toxic to larvae of the coleopteran insects *Agelastica alni* (blue alder leaf beetle) and *Leptinotarsa decemlineata* (Colorado potato beetle). *B.t. tenebrionis* makes an insecticidal crystal protein reported to be about 65–70 kilodaltons (kDa) (U.S. Pat. No. 4,766,203; see also K. Bernhard, *FEMS Microbiol. Lett.* 33, pp. 261–265 (1986).

V. Sekar et al., *Proc. Natl. Acad. Sci. USA*, 84, pp. 7036–7040 (1987), report the cloning and characterization of the gene for the coleopteran-toxic crystal protein of *B.t. tenebrionis*. The size of the protein, as deduced from the sequence of the gene, was 73 kDa, but the isolated protein contained primarily a 65 kDa component. Hofte et al., *Nucleic Acids Research*, 15, p. 7183 (1987), also report the DNA sequence for the cloned gene from *B.t. tenebrionis*, and the sequence of the gene is identical to that reported by Sekar et al. (1987).

McPherson et al., *Bio/Technology*, 6, pp. 61–66 (1988), disclose the DNA sequence for the cloned insect control gene from *B.t. tenebrionis*, and the sequence is identical to that reported by Sekar et al. (1987). *E. coli* cells and *Pseudomonas fluorescens* cells harboring the cloned gene were found to be toxic to Colorado potato beetle larvae.

A coleopteran-toxic strain, designated *B.t.* var. *san diego*, is reported by C. Herrnstadt et al., *Bio/Technology*, 4, pp. 305–308 (1986), to produce a 64 kDa crystal protein that was toxic to various coleopteran insects: strong toxicity to *Pyrrhalta luteola* (elm leaf beetle); moderate toxicity to *Anthonomus grandis* (boll weevil), *Leptinotarsa decemlineata* (Colorado potato beetle), *Otiorhynchus sulcatus* (black vine weevil), *Tenebrio molitor* (yellow mealworm) and *Haltica tombacina*; and weak toxicity to *Diabrotica undecimpunctata undecimpunctata* (western spotted cucumber beetle).

The DNA sequence of the cloned coleopteran toxin gene of *B.t. san diego* is reported in C. Herrnstadt et al., *Gene*, 57, pp. 37–46 (1987); see also U.S. Pat. No. 4,771,131, issued Sep. 13, 1988, of Herrnstadt et al. The sequence of the toxin gene of *B.t. san diego* is identical to that reported by Sekar et al. (1987) for the cloned coleopteran toxin gene of *B.t. tenebrionis*.

A. Krieg et al., *J. Appl. Ent.*, 104, pp. 417–424 (1987), report that the strain *B.t. san diego* is identical to the *B.t. tenebrionis* strain, based on various diagnostic tests.

Another new *B.t.* strain, designated EG2158, is reported by W. P. Donovan et al., *Mol. Gen. Genet.*, 214 pp. 365–372 (1988) to produce a 73 kDa crystal protein that is insecticidal to coleopteran insects. The toxin-encoding gene from *B.t.* strain EG2158 was cloned and sequenced, and its sequence is identical to that reported by Sekar et al. (1987) for the cloned *B.t. tenebrionis* coleopteran toxin gene. This coleopteran toxin gene is referred to as the cryIIIA gene by Höfte et al., *Microbiol. Rev.*, 53, pp. 242–255 (1989).

U.S. Pat. No. 4,797,279, issued Jan. 10, 1989, of D. Karamata et al., discloses a hybrid *B.t.* microorganism containing a plasmid from *B.t. kurstaki* with a lepidopteran toxin gene and a plasmid from *B.t. tenebrionis* with a coleopteran toxin gene. The hybrid *B.t.* produces crystal proteins characteristic of those made by *B.t. kurstaki*, as well as of *B.t. tenebrionis*.

European Patent Application Publication No. 0 303 379, published Feb. 15, 1989, of Mycogen Corporation, discloses a novel *B.t.* isolate identified as *B.t.* MT 104 which has insecticidal activity against both coleopteran and lepidopteran insects.

European Patent Application Publication No. 0 318 143, published May 31, 1989, of Lubrizol Genetics, Inc., discloses the cloning, characterization and selective expression of the intact partially modified gene from B.t. tenebrionis, and the transfer of the cloned gene into a host microorganism rendering the microorganism able to produce a protein having toxicity to coleopteran insects. Insect bioassay data for B.t. san diego reproduced from Herrnstadt et al., Bio/Technology, 4, pp. 305-308 (1986) discussed above, is summarized. The summary also includes data for B.t. tenebrionis, from another source; B.t. tenebrionis is reported to exhibit strong toxicity to Colorado potato beetle, moderate toxicity to western corn rootworm (Diabrotica virgifera virgifera) and weak toxicity to southern corn rootworm (Diabrotica undecimpunctata).

European Patent Application Publication No. 0 324 254, published Jul. 19, 1989, of Imperial Chemical Industries PLC, discloses a novel B.t. strain identified as A30 which has insecticidal activity against coleopteran insects.

European Patent Application Publication No. 0 328 383, published Aug. 16, 1989, of Mycogen Corporation, discloses a novel B.t. microorganism identified as B.t. PS40D1 which has insecticidal activity against coleopteran insects.

European Patent Application Publication No. 0 330 342, published Aug. 30, 1989, of Mycogen Corporation, discloses a novel B.t. microorganism identified as B.t. PS86B1 which has insecticidal activity against coleopteran insects.

These latter four publications are not prior art with respect to the present invention.

B.t. tenebrionis, first reported by A. Krieg et al., was discovered in or near Darmstadt, Germany and it is believed that B.t. san diego, reported by Herrnstadt et al., was obtained from a location in or near San Diego, Calif. B.t. strain EG2158, reported by Donovan et al., was isolated from a sample of crop dust from Kansas. Thus, various B.t. strains that have been isolated from several widely separated geographical locations all contained an apparently identical coleopteran toxin gene, the cryIIIA gene.

There appear to be no reports in the literature of any new coleopteran toxin B.t. genes other than the unique B.t. gene first discovered in B.t. tenebrionis over seven years ago.

Moreover, even among the various B.t. strains that have been reported as having crystal proteins insecticidally active against coleopteran insects, none has been shown to have significant toxicity to the larvae and adults of the insect genus Diabrotica (corn rootworm), which includes the western corn rootworm (Diabrotica virgifera virgifera), the southern corn rootworm (Diabrotica undecimpunctata howardi) and the northern corn rootworm (Diabrotica barberi). The cryIIIC gene of the present invention expresses protein toxin having quantifiable insecticidal activity against the Diabrotica insects, among other coleopteran insects.

SUMMARY OF THE INVENTION

One aspect of the present invention relates to a purified and isolated coleopteran toxin gene having a nucleotide base sequence coding for the amino acid sequence illustrated in FIG. 1 and hereinafter designated as the cryIIIC gene. The cryIIIC gene has a coding region extending from nucleotide bases 14 to 1972 shown in FIG. 1.

Another aspect of the present invention relates to the insecticidal protein produced by the cryIIIC gene. The CryIIIC protein has the amino acid sequence, as deduced from the nucleotide sequence of the cryIIIC gene from bases 14 to 1972, that is shown in FIG. 1. The protein exhibits insecticidal activity against insects of the order Coleoptera, in particular, Colorado potato beetle and insects of the genus Diabrotica.

Still another aspect of the present invention relates to a biologically pure culture of a B.t. bacterium deposited with the NRRL having Accession No. NRRL B-18533 and being designated as B.t. strain EG4961. B.t. strain EG4961 carries the cryIIIC gene and produces the insecticidal CryIIIC protein. Biologically pure cultures of other B.t. bacteria carrying the cryIIIC gene are also within the scope of this invention.

Yet another aspect of this invention relates to insecticidal compositions containing, in combination with an agriculturally acceptable carrier, either the CryIIIC protein or fermentation cultures of a B.t. strain which has produced the CryIIIC protein.

The invention also includes a method of controlling coleopteran insects by applying to a host plant for such insects an insecticidally effective amount of the CryIIIC protein or of a fermentation culture of a B.t. strain that has made the CryIIIC protein. The method is applicable to a variety of coleopteran insects, including Colorado potato beetle, elm leaf beetle, imported willow leaf beetle and corn rootworm.

Still another aspect of the present invention relates to a recombinant plasmid containing the CryIIIC gene, a biologically pure culture of a bacterium transformed with such recombinant plasmid, the bacterium preferably being B.t., as well as a plant transformed with the cryIIIC gene.

A further aspect of the present invention relates to a method of enhancing the insecticidal activity against coleopteran insects of an insecticidal composition containing a coleopteran-toxic protein, where the method comprises adding to, or incorporating into, the composition containing a CryIII protein a CryI protein in an amount effective to enhance the insecticidal activity of the composition. Insecticidal compositions containing the CryIIIC protein and a CryI protein exhibit enhanced insecticidal activity is against insects of the order Coleoptera, particularly Colorado potato beetle and corn rootworm.

BRIEF DESCRIPTION OF THE DRAWINGS

FIG. 1 comprises FIGS. 1A through 1C and shows the nucleotide base sequence of the cryIIIC gene and the deduced amino acid sequence of the CryIIIC protein. The putative ribosome binding site (RBS) is indicated. HindIII and BamHI restriction sites are also indicated.

FIG. 2 is a photograph of an ethidium bromide stained agarose gel containing size fractionated native plasmids of B.t. strains EG2158, EG2838 and EG4961. The numbers to the right of FIG. 2 indicate the approximate sizes, in megadaltons (MDa), of the plasmids of B.t. strain EG4961.

FIG. 3 is a photograph of an autoradiogram made by transferring the plasmids shown in FIG. 2 to a nitrocellulose filter, hybridizing the filter with a radioactively labeled 2.4 kilobase (kb) cryIIIB probe, and exposing the filter to X-ray film. The number to the right of FIG. 3 indicates the size, in MDa, of the plasmid of B.t. strain EG4961 that hybridizes to the cryIIIB probe. The letter "f" to the right of FIG. 3 indicates the fragments that result from the breakdown of the cryIIIB-hybridizing plasmid.

FIG. 4 is a photograph of an ethidium bromide stained agarose gel containing DNA from *B.t.* strains EG2158, EG2838 and EG4961 that has been digested with HindIII plus EcoRI and size fractionated by electrophoresis. The lane labeled "stnd" is a size standard.

FIG. 5 is a photograph of an autoradiogram made by transferring the DNA fragments of FIG. 4 to a nitrocellulose filter, hybridizing the filter with the radioactively labeled 2.4 kb cryIIIB probe, and exposing the filter to X-ray film. The numbers to the right of FIG. 5 indicate the sizes, in kb, of *B.t.* strain EG4961 restriction fragments that hybridize to the cryIIIB probe. The lane labeled "stnd" is a size standard.

DETAILED DESCRIPTION OF THE PREFERRED EMBODIMENTS

Figure 6:
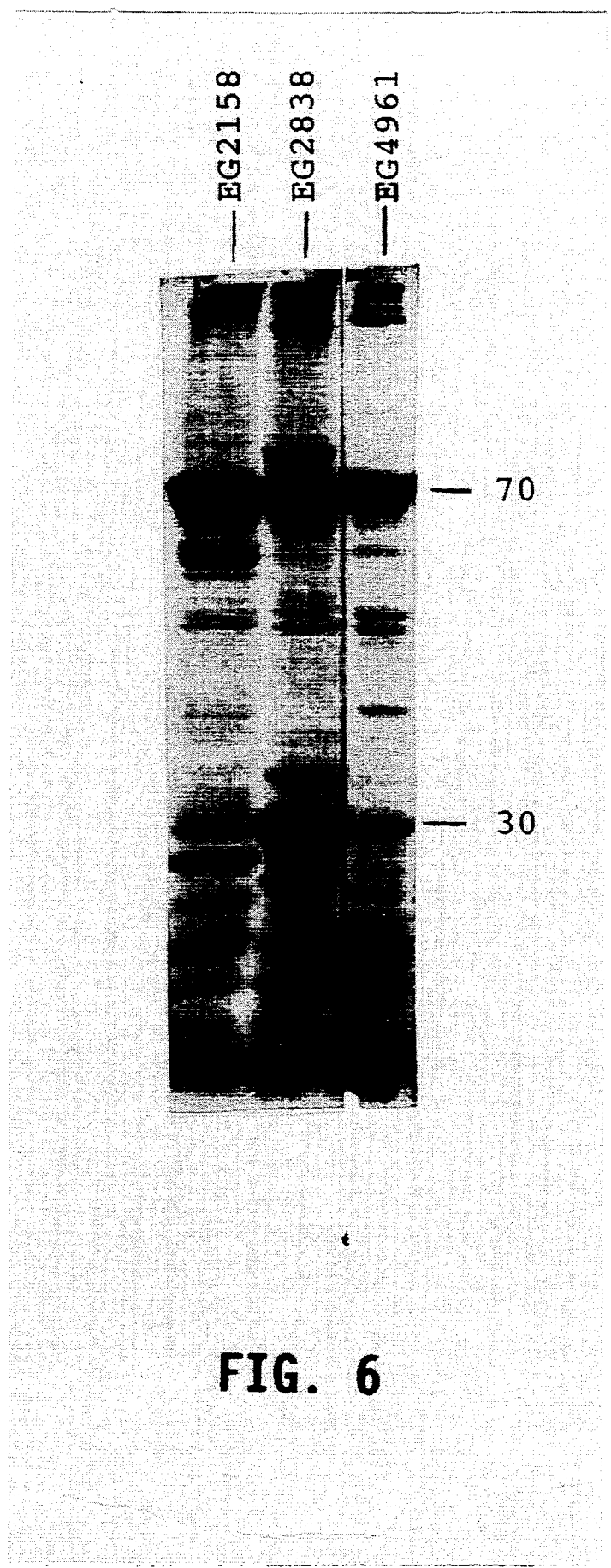
FIG. 6 is a photograph of a Coomassie stained sodium dodecyl sulfate ("SDS") polyacrylamide gel showing crystal proteins solubilized from *B.t.* strains EG2158, EG2838 and EG4961. The numbers to the right of FIG. 6 indicate the approximate sizes in kDa of the crystal proteins produced by *B.t.* strain EG4961.

The isolation and purification of the cryIIIC gene and the coleopteran-toxic CryIIIC crystal protein and the characterization of the new *B.t.* strain EG4961 which produces the CryIIIC protein are described at length in the Examples. The utility of *B.t.* strain EG4961 and of the CryIIIC crystal protein in insecticidal compositions and methods is also illustrated in the Examples.

The Examples also illustrate the synergistic enhancement of the insecticidal activity of CryIII protein by the addition of a CryI protein. Thus, insecticidal compositions having a combination of both CryIII and CryI proteins provide enhanced insecticidal activity, particularly with respect to both larvae and adult Colorado potato beetle and southern corn rootworm, as well as other insects.

The cryIII-type gene of this invention, the cryIIIC gene, has the nucleotide base sequence shown in FIG. 1. The coding region of the cryIIIC gene extends from nucleotide base position 14 to position 1972 shown in FIG. 1.

A comparison of the nucleotide base pairs of the cryIIIC gene coding region with the corresponding coding region of the prior art cryIIIA gene indicates significant differences between the two genes. The cryIIIC gene is only 75% homologous (positionally identical) with the cryIIIA gene.

A comparison of the nucleotide base pairs of the cryIIIC gene coding region with the corresponding coding region of the cryIIIB gene obtained from recently discovered *B.t.* strain EG2838 (NRRL Accession No. B-18603) indicates that the cryIIIC gene is 96% homologous (positionally identical) with the cryIIIB gene.

.The CryIII-type protein of this invention, the CryIIIC protein, that is encoded by the cryIIIC gene, has the amino acid sequence shown in FIG. 1. In this disclosure, references to the CryIIIC "protein" are synonymous with its description as a "crystal protein" "protein toxin" "insecticidal protein" or the like, unless the context indicates otherwise. The size of the CryIIIC protein, as deduced from the DNA sequence of the cryIIIC gene, is 74.4 kDa.

The size of the CryIIIB protein, as deduced from the sequence of the cryIIIB gene, is 74.2 kDa. The prior art CryIIIA protein, encoded by the cryIIIA gene, has a deduced size of 73.1 kDa.

Despite the apparent size similarity, comparison of the amino acid sequence of the CryIIIC protein with that of the prior art CryIIIA protein shows significant differences between the two. The CryIIIC protein is only 69% homologous (positionally identical amino acids) with the CryIIIA protein. The CryIIIC protein is 94% homologous with the CryIIIB protein. Nevertheless, despite the apparent homology of the CryIIIC and CryIIIB proteins, the CryIIIC protein has been shown to be a different protein than the CryIIIB protein, based on its significantly improved insecticidal activity compared to the CryIIIB protein with respect to insects of the order Coleoptera and in particular, insects of the genus Diabrotica. The CryIIIC protein is the first *B.t.* protein to exhibit quantifiable insecticidal activity against corn rootworms.

The present invention is intended to cover mutants and recombinant or genetically engineered derivatives of the cryIIIC gene that yield a coleopteran-toxic protein with essentially the same properties as the CryIIIC protein.

The cryIIIC gene is also useful as a DNA hybridization probe, for discovering similar or closely related cryIII-type genes in other *B.t.* strains. The cryIIIC gene, or portions or derivatives thereof, can be labeled for use as a hybridization probe, e.g., with a radioactive label, using conventional procedures. The labeled DNA hybridization probe may then be used in the manner described in the Examples.

The cryIIIC gene and the corresponding insecticidal CryIIIC protein were first identified in *B.t.* strain EG4961, a novel *B.t.* strain. The characteristics of *B.t.* strain EG4961 are more fully described in the Examples. Comparison of the plasmid arrays and other strain characteristics of *B.t.* strain EG4961 with those of the recently discovered *B.t.* strain EG2838 and those of the prior art *B.t.* strain EG2158 demonstrates that these three coleopteran-toxic *B.t.* strains are distinctly different.

The cryIIIC gene may be introduced into a variety of microorganism hosts, using procedures well known to those skilled in the art for transforming suitable hosts under conditions which allow for stable maintenance and expression of the cloned cryiiic gene. Suitable hosts that allow the cryIIIC gene to be expressed and the CryIIIC protein to be produced include *Bacillus thuringiensis* and other Bacillus species such as *B. subtilis* or *B. megaterium*. It should be evident that genetically altered or engineered microorganisms containing the cryIIIC gene can also contain other toxin genes present in the same microorganism and that these genes could concurrently produce insecticidal crystal proteins different from the CryIIIC protein.

The Bacillus strains described in this disclosure may be cultured using conventional growth media and standard fermentation techniques. The *B.t.* strains harboring the cryIIIC gene may be fermented, as described in the Examples, until the cultured *B.t.* cells reach the stage of their growth cycle when CryIIIC crystal protein is formed. For sporogenous *B.t.* strains, fermentation is typically continued through the sporulation stage when the CryIIIC crystal protein is formed along with spores. The *B.t.* fermentation culture is then typically harvested by centrifugation, filtration or the like to separate fermentation culture solids, containing the CryIIIC crystal protein, from the aqueous broth portion of the culture.

The *B.t.* strains exemplified in this disclosure are sporulating varieties (spore forming or sporogenous strains) but the cryIIIC gene also has utility in asporogenous Bacillus strains, i.e., strains that produce the crystal protein without production of spores. It should be understood that references to "fermentation cultures" of *B.t.* strains (containing the cryIIIC gene) in this disclosure are intended to cover sporulated *B.t.* cultures, i.e., *B.t.* cultures containing the CryIIIC crystal protein and spores, and sporogenous Bacillus strains that have produced crystal protein during the vegetative stage, as well as asporogenous Bacillus strains containing the cryIIIC gene in which the culture has reached the growth stage where crystal protein is actually produced.

The separated fermentation solids are primarily CryIIIC crystal protein and *B.t.* spores, along with some cell debris, some intact cells, and residual fermentation medium solids. If desired, the crystal protein may be separated from the other recovered solids via conventional methods, e.g., sucrose density gradient fractionation. Highly purified CryIIIC protein may be obtained by solubilizing the recovered crystal protein and then reprecipitating the protein from solution.

The CryIIIC protein, as noted earlier, is a potent insecticidal compound against coleopteran insects, such as the Colorado potato beetle, elm leaf beetle, imported willow leaf beetle, and the like. The CryIIIC protein, in contrast to the CryIIIA and CryIIIB proteins, exhibits measurable insecticidal activity against Diabrotica insects, e.g., corn rootworms, which have been relatively unaffected by other coleopteran-toxic *B.t.* crystal proteins. The CryIIIC protein may be utilized as the active ingredient in insecticidal formulations useful for the control of coleopteran insects such as those mentioned above. Such insecticidal formulations or compositions typically contain agriculturally acceptable carriers or adjuvants in addition to the active ingredient.

The CryIIIC protein may be employed in insecticidal formulations in isolated or purified form, e.g., as the crystal protein itself. Alternatively, the CryIIIC protein may be present in the recovered fermentation solids, obtained from culturing of a Bacillus strain, e.g., *Bacillus thuringiensis*, or other microorganism host carrying the cryIIIC gene and capable of producing the CryIIIC protein. Preferred Bacillus hosts include *B.t.* strain EG4961 and genetically improved *B.t.* strains derived from *B.t.* strain EG4961. The latter *B.t.* strains may be obtained via plasmid curing and/or conjugation techniques and contain the native cryIIIC gene-containing plasmid from *B.t.* strain EG4961. Genetically engineered or transformed *B.t.* strains or other host microorganisms containing a recombinant plasmid that expresses the cloned cryIIIC gene, obtained by recombinant DNA procedures, may also be used.

Examples of such transformants include *B.t.* strains EG7231 and EG7220, both of which contain the cloned cryIIIC gene on a recombinant plasmid.

The recovered fermentation solids contain primarily the crystal protein and (if a sporulating *B.t.* host is employed) spores; cell debris and residual fermentation medium solids may also be present. The recovered fermentation solids containing the CryIIIC protein may be dried, if desired, prior to incorporation in the insecticidal formulation.

The formulations or compositions of this invention containing the insecticidal CryIIIC protein as the active component are applied at an insecticidally effective amount which will vary depending on such factors as, for example, the specific coleopteran insects to be controlled, the specific plant or crop to be treated and the method of applying the insecticidally active compositions. An insecticidally effective amount of the insecticide formulation is employed in the insect control method of this invention.

The insecticide compositions are made by formulating the insecticidally active component with the desired agriculturally acceptable carrier. The formulated compositions may be in the form of a dust or granular material, or a suspension in oil (vegetable or mineral) or water or oil/water emulsions, or as a wettable powder, or in combination with any other carrier material suitable for agricultural application. Suitable agricultural carriers can be solid or liquid and are well known in the art. The term "agriculturally acceptable carrier" covers all adjuvants, e.g., inert components, dispersants, surfactants, tackifiers, binders, etc. that are ordinarily used in insecticide formulation technology; these are well known to those skilled in insecticide formulation.

The formulations containing the CryIIIC protein and one or more solid or liquid adjuvants are prepared in known manners, e.g., by homogeneously mixing, blending and/or grinding the insecticidally active CryIIIC protein component with suitable adjuvants using conventional formulation techniques.

The CryIIIC protein, and other coleopteran toxin proteins such as CryIIIB and CryIIIA, may also be used in combination with a CryI protein, to provide unexpectedly enhanced insecticidal activity against a coleopteran insect target. The coleopteran-specific activity of CryIIIC, CryIIIB and CryIIIA proteins is greatly enhanced by the addition or incorporation of a CryI protein into an insecticidal composition containing such CryIII protein. This method may be employed to make synergistic CryIII-CryI protein insecticide compositions, via physical combination of the respective CryIII and CryI proteins or via combination of *B.t.* strains making the respective proteins. The preferred CryI protein for use in the synergistic CryIII insecticide combinations is CryIA, and particularly, CryIA(c), although it is believed that other CryI proteins can also be used in the synergistic combinations. Surprisingly, there appears to be no enhancement of the CryI protein's insecticidal efficacy against lepidopteran insects; i.e., there seems to be no "reverse synergy" with CryI proteins imparted by the presence of CryIII crystal proteins.

If desired, combinations of CryIIIC (or CryIIIB) and CryI proteins in this invention may be obtained in situ in combined form, from cultures of strains of *B.t.* or other microorganism hosts carrying such cryIII genes and cryI genes capable of producing the respective CryIII and CryI proteins. Such strains or hosts may be obtained via plasmid curing and/or conjugation techniques involving *B.t.* or other strains or host microorganisms containing a recombinant plasmid that expresses the cloned cryIII and cryI genes.

An amount of CryI protein approximately equivalent to the quantity of CryIII protein present in the composition provides good enhancement of coleopteran-specific insecticidal activity. Smaller amounts of CryI protein than this 1:1 CryI:CryIII ratio will likely still give satisfactory levels of enhancement to the CryIII protein.

The insecticidal compositions of this invention are applied to the environment of the target coleopteran insect, typically onto the foliage of the plant or crop to be protected by conventional methods, preferably by spraying. Other application techniques, e.g., dusting, sprinkling, soaking, soil injection, seed coating, seedling coating or spraying, or the like, are also feasible and may be required for insects that cause root or stalk infestation. These application procedures are well known in the art.

The CryIIIC gene or its functional equivalent, hereinafter sometimes referred to as the "toxin gene," can be introduced into a wide variety of microorganism hosts. Expression of the cryIIIC gene results in the production of insecticidal CryIIIC crystal protein toxin. Suitable hosts include *B.t.* and other species of Bacillus, such as *B. subtilis* or *B. megaterium*, for example. Plant-colonizing or root-colonizing microorganisms may also be employed as the host for the cryIIIC gene. Various procedures well known to those skilled in the art are available for introducing the cryIIIC gene into the microorganism host under conditions which allow for stable maintenance and expression of the gene in the resulting transformants.

The transformants, i.e., host microorganisms that harbor a cloned gene in a recombinant plasmid, can be isolated in accordance with conventional methods, usually employing a selection technique, which allows growth of only those host microorganisms that contain a recombinant plasmid. The transformants then can be tested for insecticidal activity. Again, these techniques are standard procedures.

Characteristics of particular interest in selecting a host cell for purposes of production include ease of introducing the gene into the host, availability of expression systems, efficiency of expression, stability of the CryIIIC insecticidal protein in the host, and the presence of auxiliary genetic capabilities. The cellular host containing the insecticidal cryIIIC gene may be grown in any convenient nutrient medium, where expression of the cryIIIC gene is obtained and CryIIIC protein produced, typically to sporulation. The sporulated cells containing the crystal protein may then be harvested in accordance with conventional methods, e.g., centrifugation or filtration.

The cryIIIC gene may also be incorporated into a plant which is capable of expressing the gene and producing CryIIIC protein, rendering the plant more resistant to insect attack. Genetic engineering of plants with the cryIIIC gene may be accomplished by introducing the desired DNA containing the gene into plant tissues or cells, using DNA molecules of a variety of forms and origins that are well know to those skilled in plant genetic engineering. An example of a technique for introducing DNA into plant tissue is disclosed in European Patent Application Publication No. 0 289 479, published Nov. 2, 1988, of Monsanto Company.

DNA containing the cryIIIC gene or a modified CryIIIC gene capable of producing the CryIIIC protein may be delivered into the plant cells or tissues directly by infectious plasmids, such as Ti, the plasmid from *Agrobacterium tumefaciens*, viruses or microorganisms like *A. tumefaciens*, by the use of lysosomes or liposomes, by microinjection by mechanical methods and by other techniques familiar to those skilled in plant engineering.

Variations may be made in the CryIIIC gene nucleotide base sequences, since the various amino acids forming the protein encoded by the gene usually may be determined by more than one codon, as is well known to those skilled in the art. Moreover, there may be some variations or truncation in the coding region of the cryIIIC nucleotide base sequence which allow expression of the gene and production of functionally equivalent forms of the CryIIIC insecticidal protein. These variations which can be determined without undue experimentation by those of ordinary skill in the art with reference to the present specification are to be considered within the scope of the appended claims, since they are fully equivalent to the specifically claimed subject matter.

The present invention will now be described in more detail with reference to the following specific, non-limiting examples. The examples relate to work which was actually done based on techniques generally known in the art and using commercially available equipment.

The novel *B.t.* strain EG4961 was isolated following the procedure described in Example 1.

EXAMPLE 1

Isolation of *B.t.* Strain EG4961

Crop dust samples were obtained from various sources throughout the U.S. and abroad, typically grain storage facilities. The crop dust samples were treated by suspending the crop dust in an aqueous buffer and heating the suspension at 60° C. for 30 min. to enrich for heat resistant spore forming Bacillus-type bacteria such as *B.t.* The treated dust suspensions were diluted in aqueous buffer, and the dilutions were spread on agar plates to allow each individual bacterium from the crop dust to grow into a colony on the surface of the agar plate. After growth, a portion of each colony was transferred from the agar plate to a nitrocellulose filter. The filter was treated with NaOH to lyse the colonies and to fix the DNA from each colony onto the filter.

A modified treatment procedure was developed for use with *B.t.* colonies utilized in the colony hybridization procedure, since standard techniques applicable to *E. coli* were found to be unworkable with *B.t.* In the treatment described above, special conditions were required to assure that the *B.t.* colonies were in a vegetative state of growth, making them susceptible to lysis with NaOH. Accordingly, after a portion of each colony was transferred to the nitrocellulose filter, the filter was placed colony side up on an agar medium containing 0.5% (w/v) glucose. The transferred colonies were then allowed to grow on the agar-glucose medium for 5 hours at 30° C. Use of 0.5% glucose in the agar medium and the 5-hour, 30° C. growth cycle were critical for assuring that the *B.t.* colonies were in a vegetative state and thus susceptible to lysis.

Despite the opinion expressed by at least one researcher that attempts to use an existing coleopteran toxin gene as a probe to discover a novel gene that was toxic to the southern corn rootworm would be unsuccessful, a cloned coleopteran toxin gene was used as a specific probe to find other novel and rare coleopteran-toxic strains of *B.t.* from crop dust samples.

A 2.9 kb HindIII DNA restriction fragment containing the cryIIIA gene, formerly known as the cryC gene of *B.t.* strain EG2158, described in Donovan et al., *Mol. Gen. Genet.*, 214, pp. 365–372 (1988), was used as a probe in colony hybridization procedures.

The 2.9 kb HindIII cryIIIA DNA fragment, containing the entire cryIIIA gene, was radioactively labeled with alpha-$P^{32}$ dATP and Klenow enzyme, by standard methods. The nitrocellulose filters containing the DNA from each lysed colony were incubated at 65° C. for 16 hours in a buffered solution that contained the radioactively labeled 2.9 kb HindIII cryIIIA DNA probe to hybridize the DNA from the colonies with the DNA from the radioactively labeled cryIIIA probe. The 65° C. hybridization temperature was used to assure that the cryIIIA DNA probe would hybridize only to DNA from colonies that contained a gene that was similar to the cryIIIA DNA probe.

The 2.9 kb cryIIIA probe hybridized to many *B.t.* colonies from various samples of crop dust. Examination of these colonies revealed, unexpectedly, that they did not contain any cryIII-type genes. These colonies did contain cryI-type genes. The cryI-type genes encode lepidopteran-toxic, coleopteran-nontoxic crystal proteins with molecular masses of approximately 130 kDa. Computer-assisted comparisons of the sequence of the cryIIIA gene with the sequence of several cryI-type genes revealed that the 3'-end of the cryIIIA gene was partially homologous with portions of the cryI-type genes. This finding supported the belief that the 3'-end of the cryIIIA gene was causing the 2.9 kb cryIIIA probe to hybridize to *B.t.* colonies containing cryI-type genes.

To correct this problem, the 2.9 kb HindIII cryIIIA probe was digested with the enzyme XbaI and a 2.0 kb HindIII-XbaI fragment was purified that contained the cryIIIA gene minus its 3'-end. The 2.0 kb HindIII-XbaI fragment contains the 3'-truncated cryIIIA gene. When the 2.0 kb fragment was used in repeated colony hybridization experiments, it did not hybridize to cryI gene-containing *B.t.* colonies.

Approximately 48,000 Bacillus-type colonies from crop dust samples from various locations were probed with the radioactively labeled 2.0 kb HindIII-XbaI cryIIIA probe. Only one novel *B.t.* strain from an Illinois crop dust sample was discovered that specifically hybridized to the cryIIIA probe. That novel strain was designated *B.t.* strain EG2838, which has been deposited with the NRRL under Accession No. NRRL B-18603.

Subsequently, an additional 50,000 Bacillus-type colonies from crop dust samples were also screened with the radioactively labeled 2.0 kb HindIII-XbaI cryIIIA probe, but without success in identifying any other strains containing novel cryIII-type genes.

*B.t.* strain EG2838 was found to be insecticidally active against coleopteran insects, notably, the Colorado potato beetle. *B.t.* strain EG2838 did not have substantial insecticidal activity with respect to the southern corn rootworm. A gene, designated the cryIIIB gene, was isolated from *B.t.* strain EG2838, and its nucleotide base sequence determined. The cryIIIB gene encoded a crystal protein, designated the CryIIIB protein, containing 651 amino acids having a deduced size of 74,237 Daltons. The size of the prior art CryIIIA protein had previously been deduced to be 73,116 Daltons (644 amino acids). The cryIIIB gene is 75% homologous with the cryIIIA gene, and the CryIIIB protein is 68% homologous with the CryIIIA protein.

Approximately 40,000 Bacillus-type colonies from thirty-nine crop dust samples from various locations from around the world were screened with a cryIIIB probe obtained from *B.t.* strain EG2838. The cryIIIB probe was radioactively labeled using the procedure set forth above with respect to the radioactively labeled cryIIIA probe. The radioactively labeled cryIIIB probe consisted of a 2.4 kb SspI restriction fragment of DNA from *B.t.* strain EG2838. The fragment contains the complete protein coding region for the coleopteran toxin cryIIIB gene of *B.t.* strain EG2838. Ultimately, a novel *B.t.* strain from a crop dust sample was discovered that specifically hybridized to the cryIIIB probe. The strain was designated *B.t.* strain EG4961.

To characterize *B.t.* strain EG4961, several studies were conducted. One series of studies was performed to characterize its flagellar serotype. Additional studies were conducted to determine the sizes of the native plasmids in *B.t.* strain EG4961 and to ascertain which plasmids contained genes that encode insecticidal crystal proteins. DNA blot analysis was performed to determine whether any of the native plasmids of *B.t.* strain EG4961 hybridized with the cryIIIB probe. Also of interest was whether the cryIIIB-hybridizing DNA element of *B.t.* strain EG4961 was carried on a single naturally occurring plasmid, as opposed to being carried on multiple plasmids or on the chromosomal DNA. In addition, *B.t.* strain EG4961 was evaluated further by characterizing the crystal proteins it produced and by measuring the insecticidal activity associated with *B.t.* strain EG4961 and its crystal proteins. Examples 2 through 6 are directed to the procedures for characterizing *B.t.* strain EG4961, and Examples 8 through 12 are directed to the insecticidal activity of *B.t.* strain EG4961.

EXAMPLE 2

Characterization of the Flagellar Serotype of *B.t.* Strain EG4961

Figure 7:
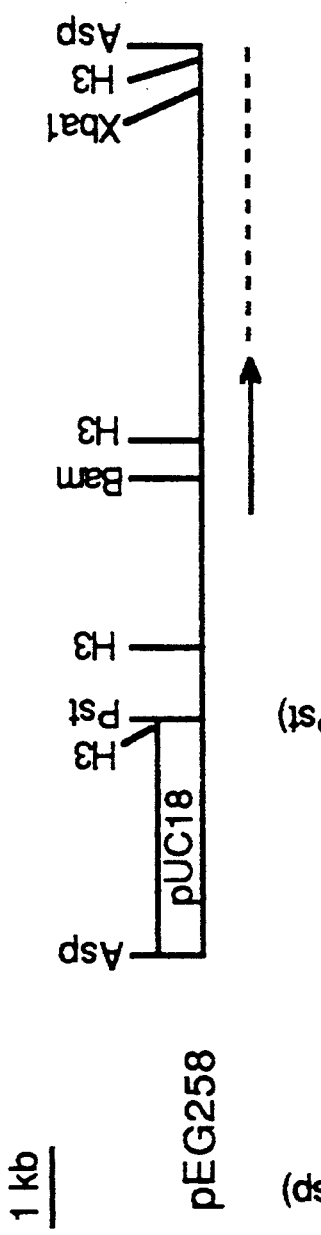
FIG. 7 shows a restriction map of plasmid pEG258. The location and orientation of the cryIIIC gene is indicated by an arrow. A gene designated the cryX gene is located within the region indicated by the dotted line. Asp stands for Asp718, Bam stands for BamHI, H3 stands for HindIII and P stands for PstI restriction enzymes. A one kb scale marker is also illustrated.

A panel of *B.t.* type-strain flagellar antibody reagents was constructed for use in serotyping investigations, using *B.t.* type-strains that are publicly available. *B.t.* type-strains HD1 (kurstaki, serotype 3ab), HD2 (thuringiensis, serotype 1), HD5 (kenyae, serotype 4ac), HD11 (aizawai, serotype 7), HD12 (morrisoni, serotype 8ab) and HD13 (tolworthi, serotype 9) were grown in liquid cultures (no shaking) under conditions that produce motile, vegetative cells. Flagellar filaments were sheared from the cells by vortexing, cells were removed by centrifugation, and flagellar filaments were collected from the supernatants on 0.2 μm pore size filters. Purified flagellar filament preparations were analyzed by sodium dodecyl sulfate polyacryamide gel electrophoresis (SDS-PAGE). The SDS-PAGE profiles for these *B.t.* type-strain flagellar filament preparations showed a major protein band for each of these preparations in the range of 20 to 35 kDa.

These purified flagellar filament preparations were used for antibody production in mice following standard procedures. The resulting antisera were screened for reaction in a standard antibody-mediated cell agglutination assay. In this assay, serial dilutions of antisera were made in a round bottomed 96-well microplate. Formalin-fixed cell suspensions of *B.t.* type-strains (or sample strains to be serotyped) were added to the wells and left undisturbed until cell mass was visible near well bottoms. Assays were scored visually for cell agglutination from the bottom of the plate using a magnifying mirror. Antisera giving the strongest specific reaction with cells of the *B.t.* type-strain from which they were derived were used as flagellar antibody reagents.

Cells from each of *B.t.* strains EG2158 and EG4961 were separately inputted as samples in a cell agglutination assay using a panel of flagellar antibody reagents from the six *B.t.* type-strains. Cells of each *B.t.* type-strain were included as controls. Results of this investigation showed that cells of HD1, HD2, HD5, HD11, HD12 and HD13, *B.t.* type-strains reacted strongly and specifically with their respective flagellar antibody reagents. *B.t.* strain EG2158 cells reacted strongly and specifically with the morrisoni (*B.t.* type-strain HD12) flagellar antibody reagent, but cells from *B.t.* strain EG4961 did not react with any of the antibody reagents. These results confirm that *B.t.* strain EG2158 is a subspecies morrisoni *B.t.* strain and indicate that *B.t.* strain EG4961 is not a subspecies morrisoni, kurstaki, thuringiensis, kenyae, aizawai or tolworthi.

EXAMPLE 3

Size Fractionation and CryIIIB Probing of Native Plasmids of EG4961

*B.t.* strains may be characterized by fractionating their plasmids according to size by the well-known procedure called agarose gel electrophoresis. The procedure involves lysing *B.t.* cells with lysozyme and SDS, electrophoresing plasmids from the lysate through an agarose gel and staining the gel with ethidium bromide to visualize the plasmids. Larger plasmids, which move more slowly through the gel, appear at the top of the gel and smaller plasmids appear toward the bottom of the gel.

The agarose gel in FIG. 2 shows that *B.t.* strain EG4961 contains native plasmids of approximately 150, 95, 70, 50, 5 and 1.5 MDa, as indicated by the dark horizontal bands. Plasmid sizes were estimated by comparison to plasmids of known sizes (not shown). FIG. 2 further shows that the coleopteran-toxic *B.t.* strain EG2838 contains native plasmids of about 100, 90 and 37 MDa. FIG. 2 also shows that the coleopteran-toxic *B.t.* strain EG2158 contains native plasmids of about 150, 105, 88, 72, and 35 MDa. Some of the plasmids, such as the 150 and 1.5 MDa plasmids of *B.t.* strain EG4961 and the 150 MDa plasmid of *B.t.* strain EG2158, may not be visible in the photograph, although they are visible in the actual gel. FIG. 2 demonstrates that the sizes of the native plasmids of *B.t.* strain EG4961 are different from the sizes of the native plasmids of *B.t.* strains EG2158 and EG2838.

The plasmids shown in FIG. 2 were transferred by blotting from the agarose gel to a nitrocellulose filter using the blot techniques of Southern, J. Molec. Biol., 98, pp. 503–517 (1975), and the filter was hybridized as described above with the radioactively labeled 2.4 kb cryIIIB DNA probe. After hybridization, the filter was exposed to X-ray film. A photograph of the X-ray film is shown in FIG. 3 which shows by the darkened area that the cryIIIB probe hybridized to the 95 MDa plasmid of *B.t.* strain EG4961. This result demonstrates that the 95 MDa plasmid of *B.t.* strain EG4961 contains a DNA sequence that is at least partly homologous to the cryIIIB gene. FIG. 3 also shows that the cryIIIB probe hybridized, as expected, to the 88 MDa plasmid of *B.t.* strain EG2158 and to the 100 MDa plasmid of *B.t.* strain EG2838. The 88 MDa plasmid of *B.t.* strain EG2158 has been previously shown to contain the coleopteran-toxin cryIIIA gene (see Donovan et al., *Mol. Gen. Genet.*, 214, pp. 365–372 (1988)). It has been determined that the 100 MDa plasmid of *B.t.* strain EG2838 contains the coleopteran toxin cryIIIB gene.

The cryIIIB probe also hybridized to small bands of DNA in each of *B.t.* strains EG4961, EG2838 and EG2158 that are indicated by the letter "f" in FIG. 3. Previous experience has shown that large *B.t.* plasmids often break into fragments during electrophoresis. These fragments normally migrate to the position of the bands indicated by the letter "f" in FIG. 3. Therefore, the bands indicated by the letter "f" in FIG. 3 are most likely derived by fragmentation of the 95 MDa, 88 MDa and 100 MDa plasmids of *B.t.* strains EG4961, EG2158 and EG2838, respectively.

EXAMPLE 4

Blot Anaylsis of DNA from *B.t.* Strain EG4961

Both chromosomal and plasmid DNA from *B.t.* strain EG4961 was extracted and digested with HindIII plus EcoRI restriction enzymes. The digested DNA was size fractionated by electrophoresis through an agarose gel, and the fragments were visualized by staining with ethidium bromide. FIG. 4 is a photograph of the stained agarose gel that contains size fractionated HindIII and ECoRI restriction fragments of *B.t.* strain EG4961. For comparison, the DNA from the coleopteran-toxic *B.t.* strains EG2158 and EG2838 was processed in an identical manner. The lane labeled "stnd" contains lambda DNA fragments of known sizes, which serve as size standards. FIG. 4 shows that HindIII plus EcoRI digested *B.t.* DNA yields hundreds of DNA fragments of various sizes.

The DNA shown in FIG. 4 was transferred from the agarose gel to a nitrocellulose filter, and the filter was hybridized at 65° C. in a buffered aqueous solution containing the radioactively labeled 2.4 kb cryIIIB DNA probe. After hybridization, the filter was exposed to X-ray film. FIG. 5 is a photograph of the X-ray film where the numbers to the right indicate the size, in kb, of the cryIIIB hybridizing fragments of *B.t.* strain EG4961 as determined by comparison with lambda DNA digested with HindIII as a size marker in the lane labeled "stnd". FIG. 5 shows that HindIII plus EcoRI digested DNA of *B.t.* strain EG4961 yields cryIIIB-hybridizing fragments of approximately 3.8 kb and 2.4 kb. FIG. 5 also shows that HindIII plus EcoRI digested DNA of *B.t.* strain EG2838 yields cryIIIB-hybridizing fragments of approximately 2.9 kb and 3.8 kb. FIG. 5 further shows that the approximate sizes of cryIIIB-hybridizing restriction DNA fragments of *B.t.* strain EG2158 are 1.6 kb and 0.7 kb.

These results suggest that *B.t.* strain EG4961 contains a cryIII-type gene that is related to the cryIIIB gene probe. The CryIIIB-hybridizing fragments of *B.t.* strain EG4961 are different from those of *B.t.* strains EG2838 and EG2158. These results and further studies described in the Examples below confirm that the cryIII-type gene of *B.t.* strain EG4961 is clearly different from the cryIIIB gene of EG2838 and the cryIIIA gene of EG2158. The cryIII-type gene of *B.t.* strain EG4961 has been designated cryIIIC.

EXAMPLE 5

Characterization of Crystal Proteins of *B.t.* Strain EG4961

*B.t.* strain EG4961 was grown in DSMG sporulation medium at 30° C. until sporulation and cell lysis had occurred (3 to 4 days growth). The DSMG medium is 0.4% (w/v) Difco nutrient broth, 25 mM $K_2HPO_4$, 25 mM $KH_2PO_4$, 0.5 mM $Ca(NO_3)_2$, 0.5 mM $MgSO_4$, 10μM $FeSO_4$, 10μM $MnCl_2$ and 0.5% (w/v) glucose. The sporulated culture of *B.t.* strain EG4961 was observed microscopically to contain free floating, irregularly shaped crystals in addition to *B.t.* spores. Experience has shown that *B.t.* crystals are usually composed of proteins that may be toxic to specific insects. The appearance of the crystals of *B.t.* strain EG4961 differed from the flat, rectangular (or rhomboidal) crystals of *B.t.* strain EG2158, but partially resembled some of the irregularly shaped crystals of *B.t.* strain EG2838.

Spores, crystals and residual lysed cell debris from the sporulated culture of *B.t.* strain EG4961 were harvested by centrifugation. The crystals were specifically solubilized from the centrifuged fermentation culture solids (containing crystals, spores and some cell debris) by heating the solids mixture in a solubilization buffer (0.13 M Tris pH 8.5, 2% (w/v) SDS, 5% (v/v) 2-mercaptoethanol, 10% (v/v) glycerol) at 100° C. for 5 min. The solubilized crystal proteins were size fractionated by SDS-PAGE. After size fractionation, the proteins were visualized by staining with Coomassie dye. Cultures of *B.t.* strains EG2158 and EG2838 are processed in an identical manner for purposes of comparison.

FIG. 6 shows the results of these analyses where the numbers to the right indicate the size, in kDa, of the crystal proteins synthesized by *B.t.* strain EG4961. A major protein of approximately 70 kDa and a minor protein of approximately 30 kDa were solubilized from centrifuged fermentation solids containing *B.t.* strain EG4961 spores and crystals. The approximately 70 kDa protein of *B.t.* strain EG4961 appears similar in size to the approximately 70 kDa coleopteran-toxic crystal protein of *B.t.* strain EG2158 and to the approximately 70 kDa coleopteran-toxic crystal protein of *B.t.* strain EG2838. The minor crystal protein of approximately 30 kDa of *B.t.* strain EG4961 is roughly similar in size to crystal proteins of approximately 31 kDa and 29 kDa produced by *B.t.* strain EG2158 and to crystal proteins of approximately 28 kDa and 32 kDa produced by *B.t.* strain EG2838. It is not known whether these small proteins are related to one another.

Following the procedure of Example 4, further DNA blot analysis revealed that the 2.4 kb cryIIIB DNA probe specifically hybridized to a single 8.3 kb Asp718-PstI restriction fragment of *B.t.* strain EG4961 DNA. This result suggested that the 8.3 kb fragment contained the complete cryIIIC gene.

The 8.3 kb Asp718-PstI fragment of *B.t.* strain EG4961 was isolated and studies were conducted on the 8.3 kb Asp718-PstI restriction fragment to confirm that the fragment contained a cryIII-type gene and to identify and determine the nucleotide base sequence of the cryIIIC gene. The procedures are set forth in Example 6.

EXAMPLE 6

Cloning and Sequencing of the cryIIIC Gene of *B.t.* Strain EG4961

To clone the 8.3 kb fragment described in the previous Example, a plasmid library of *B.t.* strain EG4961 was constructed by ligating size-selected DNA Asp718-PstI restriction fragments from *B.t.* strain EG4961 into the well-known *E. coli* vector pUC18. This procedure involved first obtaining total DNA from *B.t.* strain EG4961 by cell lysis followed by spooling, then double digesting the total DNA with both Asp718 and PstI restriction enzymes, electrophoresing the digested DNA through an agarose gel, excising a gel slice containing 7 kb-9 kb size selected fragments of DNA, and electroeluting the size selected Asp718-PstI restriction fragments from the agarose gel slice. The selected fragments were mixed with the E. Coli plasmid vector pUC18, which had also been digested with Asp718 and PstI. The pUC18 vector carries the gene for ampicillin resistance ($Amp^r$) and the vector replicates in *E. coli.* T4 DNA ligase and ATP were added to the mixture of size-selected restriction fragments of DNA from *B.t.* strain EG4961 and of digested pUC18 vector to allow the pUC18 vector to ligate with the *B.t.* strain EG4961 restriction fragments.

The plasmid library was then transformed into *E. coli* cells, a host organism lacking the gene of interest, as follows. After ligation, the DNA mixture was incubated with an ampicillin sensitive *E. coli* host strain, *E. coli* strain HB101, that had been treated with $CaCl_2$ to allow the cells to take up the DNA. *E. coli*, specifically strain HB101, was used as the host strain because these cells are easily transformed with recombinant plasmids and because *E. coli* strain HB101 does not naturally contain genes for *B.t.* crystal proteins. Since pUC18 confers resistance to ampicillin, all host cells acquiring a recombinant plasmid would become ampicillin-resistant. After exposure to the recombinant plasmids, the *E. coli* host cells were spread on agar medium that contained ampicillin. Several thousand *E. coli* colonies grew on the ampicillin-containing agar from those cells which harbored a recombinant plasmid. These *E. coli* colonies were then blotted onto nitrocellulose filters for subsequent probing.

The radioactively labeled 2.4 kb cryIIIB gene probe was then used as a DNA probe under conditions that permitted the probe to bind specifically to those transformed host colonies that contained the 8.3 kb Asp718-PstI fragment of DNA from *B.t.* strain EG4961. Twelve *E. coli* colonies specifically hybridized to the 2.4 kb cryIIIB probe. One cryIIIB-hybridizing colony, designated *E. coli* strain EG7218, was studied further. *E. coli* strain EG7218 contained a recombinant plasmid, designated pEG258, which consisted of pUC18 plus the 8.3 kb Asp718-PstI restriction fragment of DNA. The cryIIIB probe specifically hybridized to the 8.3 kb fragment of pEG258. A restriction map of pEG258 is shown in FIG. 7.

The 8.3 kb fragment of pEG258 contained HindIII fragments of 2.4 kb and 3.8 kb, and a BamHI-XbaI fragment of 4.0 kb that specifically hybridized with the cryIIIB probe. The 2.4 kb HindIII fragment was subcloned into the DNA sequencing vector M13mp18. The 4.0 kb BamHI-XbaI fragment was subcloned into the DNA sequencing vectors M13mp18 and M13mp19.

The nucleotide base sequence of a substantial part of each subcloned DNA fragment was determined using the standard Sanger dideoxy method. For each subcloned fragment, both DNA strands were sequenced by using sequence-specific 17-mer oligonucleotide primers to initiate the DNA sequencing reactions. Sequencing revealed that the 8.3 kb fragment contained an open reading frame and, in particular, a new cryIII-type gene. This new gene, designated cryIIIC, is significantly different from the cryIIIA gene. As indicated below, cryIIIC gene is also clearly distinct from the cryIIIB gene.

The DNA sequence of the cryIIIC gene and the deduced amino acid sequence of the CryIIIC protein encoded by the cryIIIC gene are shown in FIG. 1. The protein coding portion of the cryIIIC gene is defined by the nucleotides starting at position 14 and ending at position 1972. The probable ribosome binding site is indicated as "RBS" in FIG. 1A. The size of the CryIIIC protein encoded by the cryIIIC gene, as deduced from the open reading frame of the cryIIIC gene, is 74,393 Daltons (652 amino acids). It should be noted that the apparent size of the CryIIIC protein, as determined from SDS-PAGE, is approximately 70 kDa. Therefore, the CryIIIC protein will be referred to in this specification as being approximately 70 kDa in size.

The size of the prior art CryIIIA protein has previously been deduced to be 73,116 Daltons (644 amino acids). The size of the CryIIIB protein has previously been determined to be 74,237 Daltons (651 amino acids).

DNA sequencing revealed the presence of BamHI and HindIII restriction sites within the cryIIIC gene (See FIG. 1B). Knowledge of the locations of these restriction sites permitted the precise determination of the location and orientation of the cryIIIC gene within the 8.3 kb fragment as indicated by the arrow in FIG. 7.

The computer program of Queen and Korn (C. Queen and L. J. Korn, "Analysis of Biological Sequences on Small Computers," DNA, 3, pp. 421-436 (1984)) was used to compare the sequences of the cryIIIC gene to the cryIIIB and cryIIIA genes and to compare the deduced amino acid sequences of their respective CryIIIC, CryIIIB and CryIIIA proteins.

The nucleotide base sequence of the cryIIIC gene was 96% positionally identical with the nucleotide base sequence of the cryIIIB gene and only 75% positionally identical with the nucleotide base sequence of the cryIIIA gene. Thus, although the CryIIIC gene is related to the cryIIIB and cryIIIA genes, it is clear that the cryIIIC gene is distinct from the CryIIIB gene and substantially different from the cryIIIA gene.

The deduced amino acid sequence of the CryIIIC protein was found to be 94% positionally identical to the deduced amino acid sequence of the CryIIIB protein, but only 69% positionally identical to the deduced amino acid sequence of the CryIIIA protein. These differences, together with the differences in insecticidal activity as set forth below, clearly show that the CryIIIC protein encoded by the cryIIIC gene is a different protein from the CryIIIB protein or the CryIIIA protein.

Moreover, while not wishing to be bound by any theory, based on a comparison of the amino acid sequences of the CryIIIC protein and the CryIIIB protein, it is believed that the following amino acid residues may be of significance for the enhanced corn rootworm toxicity of the CryIIIC protein, where the numbers following the accepted abbreviations for the amino acids indicate the position of the amino acid in the sequence illustrated in FIG. 1: His9, His231, Gln339, Phe352, Asn446, His449, Val450, Ser451, Lys600 and Lys624. These amino acid residues were selected as being of probable significance for the corn rootworm toxicity of the CryIIIC protein because, after studying the amino acid sequences of several other CryIII proteins, the amino acids at the indicated positions fairly consistently showed different amino acids than those indicated for the CryIIIC protein.

EXAMPLE 7

Expression of the Cloned cryIIIC Gene

Studies were conducted to determine the production of the CryIIIC protein by the cryIIIC gene.

Table 1 summarizes the relevant characteristics of the *B.t.* and *E. coli* strains and plasmids used during these procedures. A plus (+) indicates the presence of the designated element, activity or function and a minus (−) indicates the absence of the same. The designations $^s$ and $^r$ indicate sensitivity and resistance, respectively, to the antibiotic with which each is used. The abbreviations used in the table have the following meanings: Amp (ampicillin); Cm (chloramphenicol); Cry (crystalliferous); Tc (tetracycline).

TABLE 1

| | Strains and Plasmids |
|---|---|
| Strain or plasmid | Relevant characteristics |
| *B. thuringiensis* | |
| HD73-26 | Cry$^-$, Cm$^s$ |
| EG7211 | HD73-26 harboring pEG220 (Cry$^-$) |
| EG7220 | HD73-26 harboring pEG260 (cryIIIC$^+$ cryX$^+$) |
| EG7231 | HD73-26 harboring pEG269 (cryIIIC$^+$ cryX$^-$) |
| EG4961 | cryIIIC$^+$ cryX$^+$ |
| *E. coli* | |
| DH5α | Cry$^-$, Amp$^s$ |
| GM2163 | Cry$^-$, Amp$^s$ |
| EG7218 | DH5α harboring pEG258 (cryIIIC$^+$ cryX$^+$) |
| EG7221 | DH5α harboring pUC18 (Cry$^-$) |
| EG7232 | DH5α harboring pEG268 (cryIIIC$^+$ cryX$^-$) |
| EG7233 | DHSα harboring pEG269 (cryIIIC$^+$ cryX$^-$) |
| Plasmids | |
| pEG220 | Amp$^r$, Tc$^r$, Cm$^r$, Cry$^-$, Bacillus-*E. coli* shuttle vector consisting of pBR322 ligated into the SphI site of pNN101 |
| pUC18 | Amp$^r$, Cry$^-$, *E. coli* vector |
| pNN101 | Cm$^r$, Tc$^r$, Cry$^-$, Bacillus vector |
| pEG258 | Amp$^r$, cryIIIC$^+$ cryX$^+$ *E. coli* recombinant plasmid consisting of the 8.3 kb Asp718-PstI cryIIIC$^+$ cryX$^+$ fragment of B.t. strain EG4961 ligated into the Asp718-PstI sites of pUC18 |
| pEG260 | Tc$^r$, Cm$^r$, cryIIIC$^+$ cryX$^+$ Bacillus recombinant plasmid consisting of the 8.3 kb Asp718-PstI cryIIIC$^+$ cryX$^+$ fragment of B.t. strain EG4961 blunt ligated into the EcoRV site of pNN101 |
| pEG268 | Amp$^r$ cryIIIC$^+$ cryX$^-$ *E. coli* recombinant plasmid consisting of a 5 kb Sau3A fragment |

TABLE 1-continued

| Strain or plasmid | Relevant characteristics |
|---|---|
| | Strains and Plasmids |
| | of B.t. strain EG4961 ligated into the BamHI site of pBR322 |
| pEG269 | Amp$^r$ (E. coli), Tc$^r$ and Cm$^r$ (B.t.), cryIIIC$^+$ cryX$^-$, recombinant shuttle plasmid consisting of pNN101 ligated into the SphI site of pEG268 |

E. coli cells harboring the cloned 8.3 kb fragment described in Example 6 were analyzed to determine if they produced the 70 kDa CryIIIC crystal protein.

Experience has shown that cloned B.t. crystal genes are poorly expressed in E. coli and highly expressed in B.t. Recombinant plasmid pEG258, constructed as set forth in Example 6, will replicate in E. coli, but not in B.t. To achieve a high level of expression of the cloned cryIIIC gene, the 8.3 kb cryIIIC fragment was transferred from pEG258 to a plasmid vector pNN101 (Tc$^r$ Cm$^r$ Cry$^-$) that is capable of replicating in B.t.

The plasmid construct pEG258 was isolated from E. coli strain EG7218 by lysozyme/SDS treatment, followed by ethanol precipitation of the plasmid DNA, all using standard procedures. The pEG258 plasmid DNA was then used to transform cells of E. coli strain GM2163 made competent by the calcium chloride procedure described earlier in Example 6. E. coli strain GM2163 is a crystal negative (Cry$^-$) and ampicillin sensitive (Amp$^s$) strain, constructed by the procedures of M. G. Marinus et al. in Mol. Gen. Genet., 192, pp. 288-289 (1983).

The plasmid construct pEG258 was again isolated, this time from the transformed E. coli strain GM 2163, using the procedures just described. The isolated pEG258 plasmid DNA was digested with Asp718 and PstI. The digested plasmid was electrophoresed through an agarose gel and the 8.3 kb Asp718-PstI CryIIIC fragment was electroeluted from the agarose gel. The 8.3 kb fragment was made blunt-ended by using T4 polymerase and deoxynucleotide triphosphates to fill in the Asp718 and PstI ends.

The blunt-ended 8.3 kb fragment was mixed with the Bacillus vector pNN101 that had been digested with EcoRV. T4 DNA ligase and ATP were added to the mixture to allow the blunt-ended 8.3 kb fragment to ligate into the EcoRV site of the pNN101 vector. After ligation, the DNA mixture was added to a suspension of B.t. strain HD73-26 cells. Cells of B.t. strain HD73-26 are crystal-negative (Cry$^-$) and chloramphenicol sensitive (Cm$^s$). Using electroporation techniques, the cells of B.t. strain HD73-26 in the mixture were induced to take up the recombinant plasmid construct, consisting of pNN101 and the ligated 8.3 kb cryIIIC fragment, also present in the mixture. Thus, the recombinant plasmid was transformed by electroporation into B.t. strain HD73-26.

After electroporation, the transformed B.t. cells were spread onto an agar medium containing 5 μg chloramphenicol and were incubated about 16-18 hours at 30° C. Cells that had taken up the plasmid pNN101 would grow into colonies on the chloramphenicol agar medium whereas cells that had not absorbed the plasmid would not grow. Cm$^r$ colonies were transferred onto nitrocellulose and then probed with the radioactively labeled cryIIIB gene and one colony, designated B.t. strain EG7220, that specifically hybridized to the cryIIIB probe was studied further.

Figure 8:
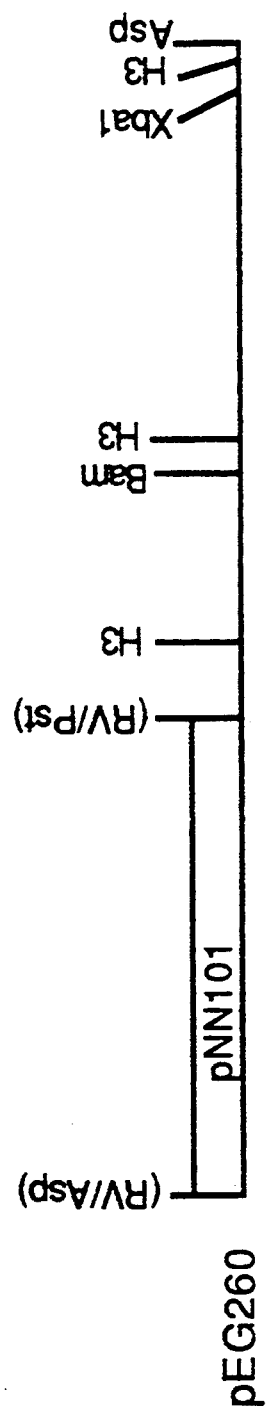
FIG. 8, aligned with and based on the same scale as FIG. 7, shows a restriction map of plasmid pEG260 containing an 8.3 kb fragment of DNA from *B.t.* strain EG4961 where the cryIIIC gene is indicated by an arrow and the cryX gene is located within the region indicated by the dotted line. In addition to the abbreviations for the restriction enzymes set forth above regarding FIG. 7, (RV/Asp) stands for the fusion of EcoRV and Asp718 restrictions sites, and (RV/Pst) stands for the fusion of EcoRV and PstI restriction sites.

EG7220 contained a plasmid, designated pEG260, that consisted of the 8.3 kb cryIIIC fragment inserted into the EcoRV site of the pNN101 vector. A restriction map of plasmid pEG260 is shown in FIG. 8.

Cells of B.t. strain EG7220 were grown in a sporulation medium containing chloramphenicol (5 μg/ml) at 23°-25° C. until sporulation and cell lysis had occurred (3-4 days). Microscopic examination revealed that the culture of B.t. strain EG7220 contained spores and free floating irregularly shaped crystals.

Spores, crystals and cell debris from the sporulated fermentation culture of B.t. strain EG7220 were harvested by centrifugation. The crystals were solubilized by heating the centrifuged fermentation solids mixture in solubilization buffer (0.13 M Tris pH 8.5, 2% (w/v) SDS, 5% (v/v) 2-mercaptoethanol, 10% (v/v) glycerol) at 100° C. for 5 min. After heating, the mixture was applied to an SDS-polyacryamide gel and proteins in the mixture were size fractionated by electrophoresis. After size fractionation, the proteins were visualized by staining with Coomassie dye. A photograph of the Coomassie stained gel is shown in FIG. 10.

Figure 10:
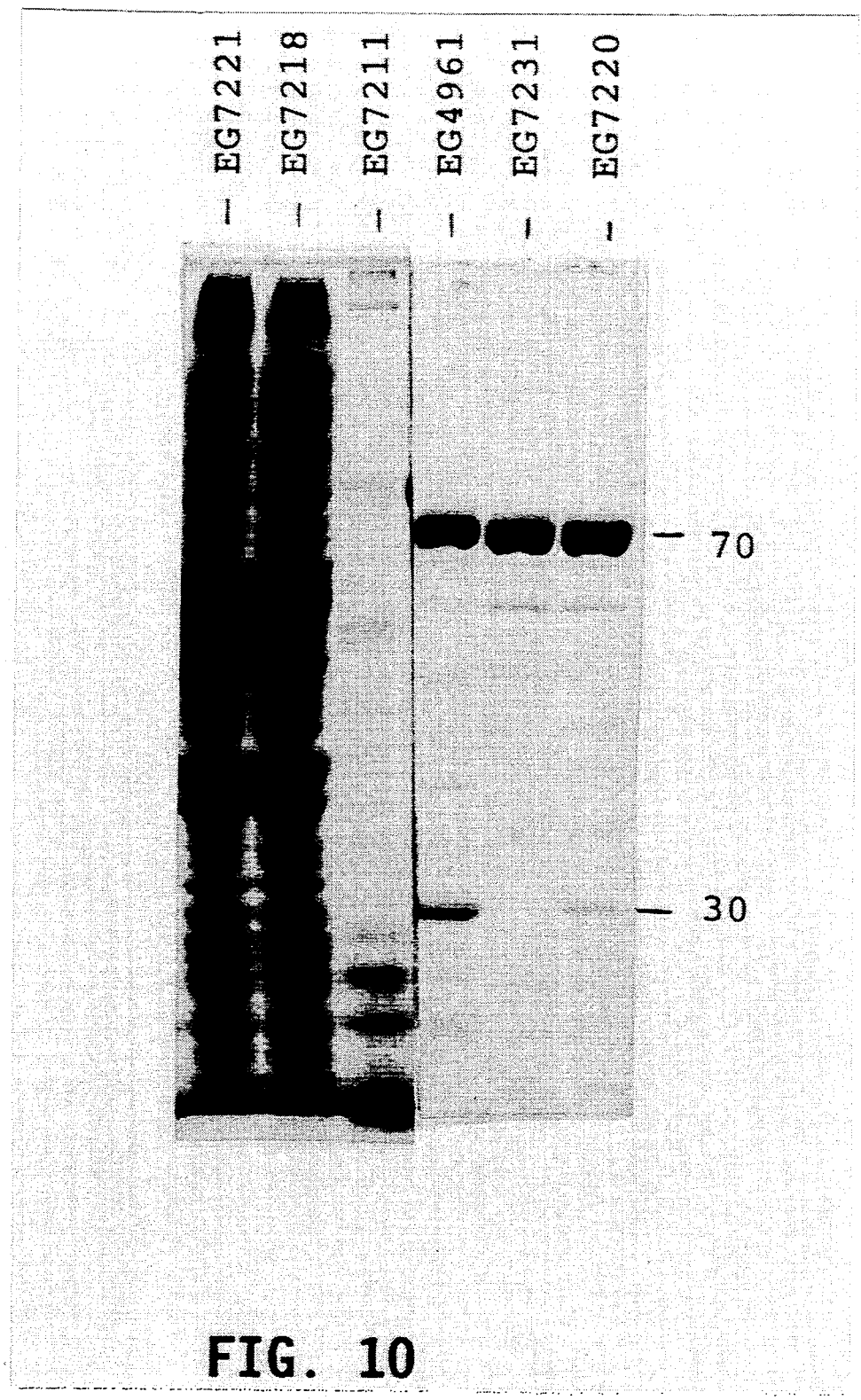
FIG. 10 is a photograph of a Coomassie stained SDS-polyacrylamide gel. The gel shows protein bands synthesized by the following bacterial strains: *E. coli* strain EG7221(pUC18/Cry−); *E. coli* strain EG7218-(pEG258/CryIIIC+ cryX+); *B.t.* strain EG7211-(pEG220/Cry−); *B.t.* strain EG4961(cryIIIC+cryX+); *B.t.* strain EG7231(pEG269/CryIIIC+ cryX−); and *B.t.* strain EG7220(pEG260/cryIIIC+ cryX+). The numbers to the right of the gel indicate approximate sizes, in kDa, of the crystal proteins produced by these strains.

FIG. 10 shows that B.t. strain EG7220 produced a major protein of approximately 70 kDa and a minor protein of approximately 30 kDa. These proteins appeared to be identical in size with the major approximately 70 kDa protein and the minor approximately 30 kDa protein produced by B.t. strain EG4961 (FIG. 10). This result demonstrates that the 8.3 kb fragment of pEG260 contains two crystal protein genes: one for the approximately 70 kDa protein and one for the approximately 30 kDa protein.

The gene encoding the approximately 70 kDa protein is the cryIIIC gene, and the encoded protein is the CryIIIC protein. The gene encoding the approximately 30 kDa crystal protein has been designated cryX, and the encoded protein has been designated CryX.

As expected and as illustrated in FIG. 10, an isogenic control strain of B.t., designated EG7211, consisting of B.t. strain HD73-26 and harboring only the plasmid vector pEG220, did not produce the approximately 70 kDa protein or the approximately 30 kDa protein. Plasmid pEG220 is an ampicillin resistant, tetracycline resistant, chloramphenicol resistant and crystal-negative E. coli-Bacillus shuttle vector consisting of pBR322 ligated into the SphI site of pNN101.

E. coli cells harboring the cloned 8.3 kb fragment containing the cryIIIC gene and the cryX gene were analyzed to determine whether they produced the approximately 70 kDa and approximately 30 kDa crystal proteins. E. coli cells harboring pEG258, designated strain EG7218, were grown to late stationary phase and cells were harvested by centrifugation. E. coli strain EG7218 cells were lysed and total cellular proteins were solubilized by heating the cells in the protein buffer. The complement of proteins solubilized from E. coli EG7218 cells appeared identical to the complement of proteins solubilized from a negative control strain of E. coli, designated EG7221, that harbored only the plasmid vector pUC18 as illustrated in FIG. 10. This result demonstrates that E. coli cells harboring the cloned 8.3 kb cryIIIC fragment produce very little, if any, of either the approximately 70 kDa or the approximately 30 kDa crystal proteins.

The following procedures were used to isolate the cryIIIC gene, responsible for making the approximately 70 kDa CryIIIC protein.

A Sau3A fragment of DNA from *B.t.* strain EG4961 that contained the cryIIIC gene, but not the cryX gene, was cloned by using the cryIIIB gene as a probe. This was accomplished by partially digesting DNA from *B.t.* strain EG4961 with Sau3A, electrophoresing the digested DNA through an agarose gel and excising a gel slice containing Sau3A fragments of 4 kb to 9 kb. The Sau3A fragments were electroeluted from the gel slice and mixed with plasmid pBR322 vector that had been digested with BamHI. The Sau3A fragments were ligated with the pBR322 vector. The ligation mix was incubated with CaCl$_2$-treated cells of *E. coli* strain DH5α to allow the cells to take up plasmid DNA.

After incubation, the cells were plated on agar plates containing ampicillin and LB medium (1% (w/v) Difco tryptone, 0.5% (w/v) Difco yeast extract, 0.5% (w/v) NaCl, pH 7.0), to select for those cells that had absorbed plasmid DNA. Several hundred Amp$^r$ transformant colonies were blotted onto nitrocellulose filters and the filters were probed with the radioactively labeled cryIIIB probe as described above in Example 1. The probe hybridized to several colonies and the characterization of one of these colonies, designated EG7232, is further described here. E. coli strain EG7232 contained a plasmid, designated pEG268, that consisted of pBR322 plus an inserted Sau3A-BamHI DNA fragment of approximately 5 kb. The inserted DNA fragment specifically hybridized to the radioactively labeled cryIIIB probe.

Figure 9:
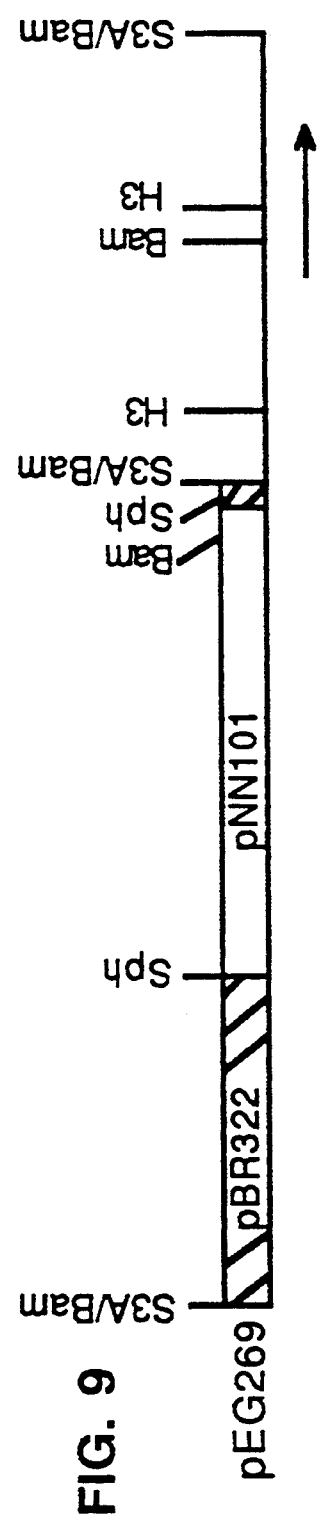
FIG. 9, aligned with and based on the same scale as FIG. 7, shows a restriction map of plasmid pEG269 containing the cryIIIC gene as indicated by an arrow, as part of a fragment of DNA from recombinant *E. coli* strain EG7233. The abbreviations used with regard to pEG258 illustrated in FIG. 7 are applicable to this figure. In addition, Sph stands for the SphI restriction site, and S3A/Bam stands for the fusion of SauIIIA and BamHI restriction sites.

Plasmid pEG268 (Amp$^r$ Tc$^s$) will replicate in *E. coli* but not in *B.t.* To obtain a derivative of pEG268 that could replicate in *B.t.*, pEG268 was digested with SphI, mixed with the Bacillus plasmid pNN101 (CM$^r$Tc$^r$) that had also been digested with SphI and the mixture was ligated. The ligation mixture was incubated with a suspension of CaCl$_2$-treated *E. coli* cells to allow the cells to take up DNA from the pEG268 plasmid ligated with pNN101. After incubation, the cells were plated on agar plates containing LB medium and tetracycline, and several hundred tetracycline resistant colonies grew. Only those cells that had absorbed a plasmid consisting of pEG268 and pNN101 would be able to grow and form colonies in the presence of tetracycline. The characterization of one of these Tc$^r$ colonies, designated EG7233, was selected for further study. As expected, *E. coli* strain EG7233 was found to contain a plasmid, designated pEG269, that consisted of pNN101 inserted into the SphI site of pEG268. A restriction map of pEG269 is shown in FIG. 9.

The plasmid construct pEG269 was isolated from *E. coli* strain EG7233 by lysozyme/SDS treatment, followed by ethanol precipitation of the plasmid DNA, all using standard procedures. The pEG269 plasmid DNA was then used to transform cells of *E. coli* strain GM2163 made competent by the calcium chloride procedure, all as described earlier.

The plasmid construct pEG269 was again isolated, this time from the transformed *E. coli* strain GM2163. The isolated pEG269 plasmid DNA was added to a suspension of cells of the crystal-negative, chloramphenicol-sensitive *B.t.* strain HD73-26 and an electric current was passed through the mixture, such that pEG269 was transformed by electroporation into *B.t.* strain HD73-26. The cells were plated onto an agar plate containing LB medium and chloramphenicol and, after incubation, several hundred Cm$^r$ colonies grew. The characterization of one of these Cm$^r$ colonies, designated EG7231, was selected for investigation. As expected, *B.t.* strain EG7231 was found to contain pEG269.

Cells of *B.t.* strain EG7231 were grown in DSMG medium containing chloramphenicol at 20°-23° C. for 4 days. Microscopic examination showed that the culture contained, in addition to spores, particles that resembled *B.t.* crystals. The culture solids including spores, crystals and cell debris were harvested by centrifugation and suspended in an aqueous solution at a concentration of 100 mg of culture solids/ml. A portion of this suspension was mixed with solubilization buffer (0.13 M Tris pH 8.5, 2% w/v SDS, 5% v/v 2-mercapto-ethanol, 10% v/v glycerol), heated at 100° C. for 5 minutes and the mixture was electrophoresed through an SDS-polyacrylamide gel to size fractionate proteins. After size fractionation, the proteins were visualized by staining the gel with Coomassie dye. A photograph of the stained gel is included in FIG. 10.

*B.t.* strain EG7231 produced a major protein of approximately 70 kDa that appeared to be identical in size to the approximately 70 kDa CryIIIC protein produced by *B.t.* strain EG4961, as indicated in FIG. 10. *B.t.* strain EG7231 did not produce any detectable amount of the approximately 30 kDa crystal protein (FIG. 10). This result demonstrates that the cryX gene for the approximately 30 kDa crystal protein is located within the region indicated by the dotted line in FIGS. 7 and 8. Furthermore, this shows that *B.t.* strain EG7231 contains the cryIIIC gene in isolated form.

The following Examples 8–12 describe the manner in which the insecticidal activity of *B.t.* strain EG4961 and of the CryIIIC protein was determined.

Insecticidal Activity of *B.t.* Strain EG4961 and the CryIIIC Protein Compared to *B.t.* Strain EG2158, *B.t. tenebrionis* and the CryIIIA Protein

EXAMPLE 8

General Preparation and Testing Procedures for Insecticidal Bioassays

Fermentation concentrates. *B.t.* strains EG4961 and EG2158 and *B.t. tenebrionis* ("*B.t. t.*") were grown in a liquid sporulation medium at 30° C. until sporulation and lysis had occurred. The medium contained a protein source, a carbohydrate source, and mineral salts and is typical of those in the art. NaOH was added to adjust the medium to pH 7.5 prior to autoclaving. The fermentation broth was concentrated by centrifugation and refrigerated until use.

As used herein, "CryIII" crystal protein designates the crystal protein of approximately 70 kDa obtained from the cultures of each of *B.t.* strains EG4961 and EG2158 and *B.t.t.* being tested. The CryIII crystal proteins were purified from the fermentation culture solids using sucrose density gradients. When using sucrose density gradients to separate the components of the fermentation culture of sporulated *B.t.*, *B.t.* spores form a pellet at the bottom of the gradient and *B.t.* crystals form a band at approximately the middle of the gradient. Thus, sucrose density gradients permit the separation of *B.t.* crystal proteins, in relatively pure form, from *B.t.* spores and other fermentation culture solids. The separated CryIII crystal proteins were stored at 4° C. until use.

Quantification of the amount of CryIII crystal protein in all samples bioassayed was determined using standard SDS-PAGE techniques. The following insects were tested:

southern corn rootworm (SCRW) *Diabrotica undecimpunctata howardi* western corn rootworm (WCRW) *Diabrotica virgifera virgifera*

Colorado potato beetle (CPB) *Leptinotarsa decemlineata* elm leaf beetle *Pyrrhalta luteola* imported willow leaf beetle *Plagiodera versicolora*

Two types of bioassays were performed, one using an artificial diet and the other using a leaf dip.

Artificial diet bioassays. SCRW larvae were bioassayed via surface contamination of an artificial diet similar to Marrone et al., *J. Econ. Entomol.*, 78, pp. 290–293 (1985), but without formalin. Each bioassay consisted of eight serial aqueous dilutions with aliquots applied to the surface of the diet. After the diluent (an aqueous 0.005% Triton ® X-100 solution) had dried, first instar larvae were placed on the diet and incubated at 28° C. Thirty-two larvae were tested per dose. Mortality was scored after 7 days. Data from replicated bioassays were pooled for probit analysis (R. J. Daum, *Bull. Entomol. Soc. Am.*, 16, pp. 10–15 (1970)) with mortality corrected for control death, the control being the diluent only (W. S. Abbott, *J. Econ. Entomol.*, 18, pp. 265–267 (1925)). Results are reported by amount of CryIII crystal protein per $mm^2$ of diet surface resulting in $LC_{50}$, the concentration killing 50% of the test insects. 95% confidence intervals are reported within parentheses.

First instar WCRW larvae were tested on the same artificial diet at one dose. Mortality was read at 48 hours.

First instar CPB larvae were tested using similar techniques, except for the substitution of BioServe's #9380 insect diet with potato flakes added for the artificial diet. Mortality was scored at three days instead of seven days.

Leaf dip bioassays. For insect species or stages where suitable artificial diets were not available, bioassays were conducted by dipping suitable natural food materials (leaves) into known treatment concentrations suspended in an aqueous 0.2% Triton ® X-100 solution. After excess material had dripped off, the leaves were allowed to dry. Leaves dipped in 0.2% Triton ® X-100 served as untreated controls. Five or ten insects were confined in a petri dish with a treated leaf and allowed to feed for 48 hours. SCRW adults, CPB adults, elm leaf beetle larvae and adults, and imported willow leaf beetle larvae and adults were tested in this manner using appropriate food sources.

Any deviations from the above methodologies are noted with the appropriate data.

EXAMPLE 9

Insecticidal activity of cryIII proteins against CPB larvae, elm leaf beetles and imported willow leaf beetle larvae

*B.t.* strain EG4961 is similar in activity to the previously discovered *B.t.* strain EG2158 against CPB larvae when tested on artificial diet, as shown by the data in Table 2.

TABLE 2

Insecticidal activity of B.t. strains EG4961 and EG2158 against first instar Colorado potato beetle larvae in artificial diet bioassays

| Sample Type | Assays | $LC_{50}$ (95% C.I.)* in ng CryIII/$mm^2$ | |
|---|---|---|---|
| | | EG4961 | EG2158 |
| Ferm. conc. | 2 | 0.47 (0.39–0.57) | 0.42 (0.35–0.50) |
| Control mortality | | 3.1% | |

*95% confidence interval set forth in parentheses

Leaf dip bioassays have also demonstrated that *B.t.* strain EG4961 is similar in activity to *B.t.* strain EG2158 and *B.t.t.* against elm leaf beetle larvae and adults and imported willow leaf beetle larvae.

EXAMPLE 10

Insecticidal activity of *B.t.* strains and cryIII Proteins against SCRW larvae in artificial diet bioassays

*B.t.* strain EG4961 possesses unique activity against SCRW larvae compared to *B.t.* strain EG2158 and *B.t.t.* in artificial diet bioassays, as shown by the bioassay data in Table 3. The comparisons in Table 3 labeled "Ferm. conc. #1" and "Ferm. conc. #2" were based on different fermentation concentrates of *B.t.* strain EG4961. Neither *B.t.* strain EG2158 nor *B.t.t.* caused over 15% mortality at the highest dose tested. In contrast, $LC_{50}$ values (i.e., 50% mortality at the specified dose) were obtained for *B.t.* strain EG4961 (Table 3).

When the purified CryIIIC crystal protein of *B.t.* strain EG4961 was bioassayed, the activity observed was only slightly less than that obtained with *B.t.* strain EG4961 fermentation concentrates (containing spores and crystals). This result identified the CryIIIC crystal protein as the toxic agent in *B.t.* strain EG4961. Surviving larvae in the *B.t.* strain EG4961 bioassays (both fermentation concentrates and purified crystal protein) were extremely stunted in growth compared to the untreated control larvae.

What little activity the fermentation concentrate of *B.t.* strain EG2158 had against SCRW larvae was lost when its purified CryIIIA crystal protein was assayed alone. Even with the concentration of purified CryIIIA protein increased five-fold over the corresponding amount of CryIIIC crystal protein, SCRW activity was non-existent for the CryIIIA protein. The minimal activity of *B.t.* strain EG2158 as a fermentation concentrate may have been dependent on the presence of spores along with the CryIIIA crystal protein.

TABLE 3

Insecticidal activity of B.t. strain EG4961 against SCRW larvae in artificial diet bioassays

| Sample type | # assays | $LC_{50}$ (95% C.I.) in ng CryIII/$mm^2$ | | |
|---|---|---|---|---|
| | | EG4961 | EG2158 | B.t.t. |
| Ferm. conc. #1 | 4 | 170 (139–213) | 14% dead @ 1000 | not tested |
| Control mortality #1 | | 9.4% | | |
| Ferm. conc. #2 | 4 | 206 (161–273) | not tested | 15% dead @ 1000 |
| Control mortality #2 | | 8.6% | | |
| Purified protein crystals | 4 | 645 (521–819) | 3% dead @ 5000 | not tested |
| Control mortality | | 8.3% | | |

An artificial diet bioassay testing *B.t.* strain EG4961 fermentation concentrate at one dose against WCRW larvae yielded mortality similar to that observed with SCRW larvae. As with SCRW larvae, *B.t.t.* yielded little mortality greater than the control.

EXAMPLE 11

Insecticidal activity of *B.t.* strains EG4961, EG2158 and *B.t.t.* against adult SCRW and adult CPB in leaf dip bioassays In addition to its unique activity against SCRW larvae, *B.t.* strain EG4961 also exhibits unique insecticidal activity to adult stages of both SCRW and CPB (Table 4) which are relatively unaffected by *B.t.* strain EG2158 or *B.t.t.* Insect bioassay data from these studies are shown in Table 4.

TABLE 4

Insecticidal activity of B.t. strains EG4961, EG2158 and B.t.t. against adult SCRW and adult CPB in leaf dip bioassays

| Strain | μg CryIII/ml | % dead at 48 hrs. SCRW | CPB |
|---|---|---|---|
| EG4961 | 2800 | 50 | 100 |
|  | 1400 | 37.5 | 98 |
|  | 700 | 25 | 95 |
|  | 350 | 10 | 70 |
| EG2158 | 4350 | — | — |
|  | 2175 | — | 0 |
|  | 1088 | — | 10 |
|  | 544 | — | — |
| B.t.t. | 2250 | 0 | 0 |
|  | 1125 | 10 | 5 |
|  | 563 | 0 | 0 |
| Control mortality |  | 0 | 0 |

(—) dashes indicate not tested.

EXAMPLE 12

Insecticidal activity of the cloned cryIIIC gene

*B.t.* strain EG4961 and recombinant *B.t.* strain EG7231, containing the cloned cryIIIC gene from *B.t.* strain EG4961.and described in Example 7, were grown on liquid sporulation medium and concentrated via centrifugation as described generally in Examples 5 through 7. Both concentrates were bioassayed against SCRW larvae and CPB larvae on artificial diet using previously described techniques but with three doses instead of eight and (for CPB) 16 CPB larvae per dose instead of 32. The results set forth in Table 5 demonstrate that *B.t.* strain EG7231 produces a CryIIIC crystal protein equal in toxicity to that found in *B.t.* strain EG4961. The crystal negative, sporulating *B.t.* strain EG7211 used to create *B.t.* strain EG7231 was tested as an additional control and was not active. This bioassay verifies that the cryIIIC gene produces the coleopteran-active crystal protein in *B.t.* strain EG4961.

TABLE 5

Activity of B.t. strains EG7231 and EG4961 against SCRW larvae and CPB larvae in artificial diet bioassays

| Strain | LC$_{50}$ ng CryIII/mm$^2$ (95% C.I.) SCRW | CPB |
|---|---|---|
| EG7231 | 359 (238–593) | 0.23 (0.05–0.49) |
| EG4961 | 421 (253–1086) | 0.32 (0.19–0.50) |
| EG7211 | 9.4% dead | 12.5% dead |
| Control | 6.25% dead | 3.125% dead |

The following Example 13 relates to studies in which the insecticidal activity of CryIII proteins against coleopteran insects is demonstrably enhanced by the combination of a CryI protein with a CryIII protein. CryIA(c) protein crystals are not toxic to coleopteran insects, but are known to be active against numerous species of lepidopteran insects.

EXAMPLE 13

Synergistic Enhancement of Insecticidal Activity of CryIII Protein by. Adding CryI Protein A recombinant *B.t.* strain, EG1269, producing only CryIA(c) protein crystals, was grown on liquid sporulation media using the techniques described above generally in Examples 5–7. Recombinant *B.t.* strain EG1269 was constructed by introducing plasmid pEG157 into *B.t.* strain HD73-26. Plasmid pEG157 was made by subcloning the cryIA(c) gene from pEG87 (*B.t.* strain HD263-6), into the shuttle vector pEG147. The CryIA(c) protein crystals were purified by Renografin gradient and quantified using the SDS-PAGE method mentioned previously. An equal amount of these CryI crystals was added to CryIIIC crystals and the crystal protein mixture was bioassayed on artificial diet against SCRW larvae. The CryIIIC-CryI protein mixture was significantly more toxic than the CryIIIC crystals alone, as is clearly indicated by the data in Table 6.

TABLE 6

Insecticidal activity of a mixture of CryIIIC and CryIA(c) crystal proteins against SCRW larvae in an artificial diet bioassay

| Treatment | # assays | LC$_{50}$ ng CryIIIC/mm$^2$ (95% C.I.) |
|---|---|---|
| CryIIIC crystals | 2 | 1180 (810–2000) |
| CryIIIC crystals + CryIA(c) crystals | 2 | 309 (220–500) |
| CryIA(c) crystals | 2 | 15.6% dead at 571 ng/mm$^2$ |
| Control mortality |  | 6.25% |

To assure the availability of materials to those interested members of the public upon issuance of a patent on the present application deposits of the following microorganisms were made prior to the filing of present application with the ARS Patent Collection, Agricultural Research Culture Collection, Northern Regional Research Laboratory (NRRL), 1815 North University Street, Peoria, Ill. 61604, as indicated in the following Table 7:

TABLE 7

| Bacterial Strain | NRRL Accession No. | Date of Deposit |
|---|---|---|
| *B. thuringiensis* EG2158 | B-18213 | April 29, 1987 |
| *B. thuringiensis* HD73-26 | B-18508 | June 12, 1989 |
| *B. thuringiensis* EG4961 | B-18533 | September 13, 1989 |
| *B. thuringiensis* EG2838 | B-18603 | February 8, 1990 |
| *B. thuringiensis* EG7231 | B-18627 | February 28, 1990 |
| *E. coli* EG7218 | B-18534 | September 13, 1989 |

These microorganism deposits were made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application.

The present invention may be embodied in other specific forms without departing from the spirit or essential attributes thereof and, accordingly, reference should be made to the appended claims, rather than to the foregoing specification as indicating the scope of the invention.

We claim:

1. An isolated coleopteran-toxic protein having the amino acid sequence illustrated in FIG. 1.

2. An insecticide composition comprising an insecticidally effective amount of the protein of claim 1 and an agriculturally acceptable carrier.

3. The insecticide composition of claim 2 wherein the coleopteran-toxic protein is contained in a *Bacillus thuringiensis* bacterium.

4. An insecticide composition useful against coleopteran insects comprising the coleopteran-toxic protein of claim 1 and a CryI protein, the CryI protein being present in an amount effective to enhance the insecticidal activity of the composition against coleopteran insects.

5. The composition of claim 4 wherein the CryI protein is CryIA protein.

6. The composition of claim 4 wherein the CryI protein is CryIA(c) protein.

7. The composition of claim 4 wherein the coleopteran-toxic protein and CryI protein are present in approximately equal amounts.

* * * * *